United States Patent [19]
Harris et al.

[11] Patent Number: 5,721,230
[45] Date of Patent: Feb. 24, 1998

[54] SUBSTITUTED PYRROLES

[75] Inventors: William Harris, Welwyn; Christopher Huw Hill, Knebworth; Geoffrey Lawton, Hitchin, all of England

[73] Assignee: Hoffmann-La Roche Inc., Nutley, N.J.

[21] Appl. No.: 644,656

[22] Filed: Apr. 24, 1996

Related U.S. Application Data

[63] Continuation of Ser. No. 362,365, Dec. 22, 1994, abandoned, which is a continuation-in-part of Ser. No. 223,291, Apr. 5, 1994, abandoned.

[30] Foreign Application Priority Data

May 10, 1993 [GB] United Kingdom .................. 9309602
Feb. 21, 1994 [GB] United Kingdom .................. 9403249

[51] Int. Cl.$^6$ .................. A61K 31/435; C07D 463/00
[52] U.S. Cl. .................................. 514/214; 546/94
[58] Field of Search ........................ 514/214; 546/94

[56] References Cited

U.S. PATENT DOCUMENTS

| | | | |
|---|---|---|---|
| 4,912,107 | 3/1990 | Kleinschroth et al. | 514/232.5 |
| 5,057,614 | 10/1991 | Davis et al. | 548/466 |
| 5,292,747 | 3/1994 | Davis | 514/285 |
| 5,380,746 | 1/1995 | Barth | 514/414 |
| 5,545,636 | 8/1996 | Heath | 514/214 |

FOREIGN PATENT DOCUMENTS

| | | |
|---|---|---|
| 9050033 | 2/1990 | Australia . |
| 0328000 | 2/1989 | European Pat. Off. . |
| 0328026 | 8/1989 | European Pat. Off. . |
| 0362695 | 9/1989 | European Pat. Off. . |
| 384 349 | 2/1990 | European Pat. Off. . |
| 470 490 | 7/1991 | European Pat. Off. . |
| 540 956 | 10/1992 | European Pat. Off. . |

OTHER PUBLICATIONS

McOmie "Protective groups in organic chemistry" pp. 56–57, 1974.
Tetrahedron 1991, 47(26), pp. 4645–4664.
FEBS Lett. 1991 293(1–2), pp. 169–172.
Biochem. Soc. Trans. 1993, 21(4) 384S.
Biochem. J. 1993, 294(2) pp. 335–337.
Takai, et al. BBRC 19, 1218 (1979).
Kikkawa et al. J. Biol. Chem. 257, 13341 (1982).
Nixon et al. Novel Potent and Selective inhibitors of PKC, Show Antiinflammatory Activity, Drug Exptl. Clin. Res. XVII pp. 389–393 (1991).
Bit et al., Inhibitors of PKC, 3 Potent and Highly Selective, J. Med. Chem. 36 pp. 21–29 (1993).
McOmie, Protective Groups In Organic Chemistry, pp. 56–60 (1973).
Mulqueen et al., Agents Actions 37(1992) pp. 85–89.

*Primary Examiner*—Ceila Chang
*Attorney, Agent, or Firm*—George W. Johnston; Patricia S. Rocha-Tramaloni; Robert A. Silverman

[57] ABSTRACT

Compounds of the formula

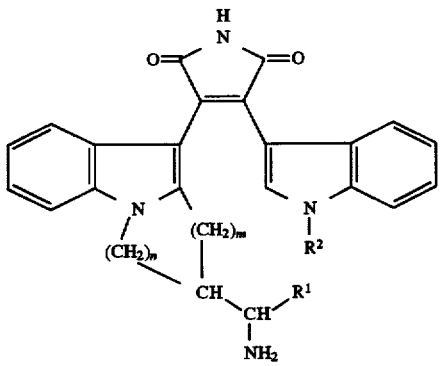

wherein $R^1$ is lower alkyl, lower cycloalkyl, aryl or lower aralkyl;

$R^2$ is hydrogen, aryl or lower alkyl optionally substituted by hydroxy, acyloxy, amino, mono(lower alkyl)amino, di(lower alkyl)amino, carboxy, lower alkoxycarbonyl or aminocarbonyl; and m and n are, independently, the numerals 1 or 2, and pharmaceutically acceptable salts of acidic compounds of formula I with bases and of basic compounds of formula I with acids are useful in the control or prevention of illnesses, particularly, in the control or prevention of inflammatory, immunological, oncological, bronchopulmonary, dermatological and cardiovascular disorders, in the treatment of asthma, AIDS or diabetic complications or for the stimulation of hair growth.

23 Claims, No Drawings

SUBSTITUTED PYRROLES

This is a continuation of application Ser. No. 08/362,365, filed Dec. 22, 1994, now abandoned, which is a Rule 60 Continuation of Ser. No. 08/223,291, filed Apr. 5, 1994 now abandoned.

BRIEF SUMMARY OF THE INVENTION

The invention relates to substituted pyrroles. More particularly, the invention relates to compounds of the formula I

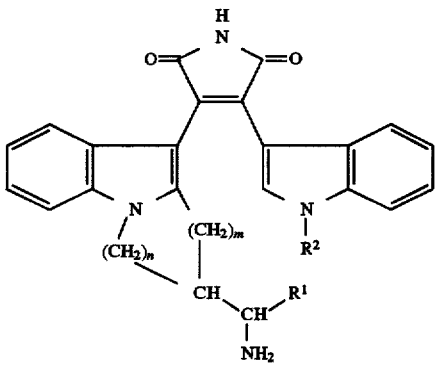

wherein $R^1$ is lower alkyl, lower cycloalkyl, aryl or lower aralkyl;

$R^2$ is hydrogen, aryl or lower alkyl optionally substituted by hydroxy, acyloxy, amino, mono(lower alkyl)amino, di(lower alkyl)amino, carboxy, lower alkoxycarbonyl or aminocarbonyl; and m and n are, independently, the numerals 1 or 2, and pharmaceutically acceptable salts of acidic compounds of formula I with bases and of basic compounds of formula I with acids.

DETAILED DESCRIPTION OF THE INVENTION

The invention relates to substituted pyrroles. More particularly, the invention relates to compounds of formula I

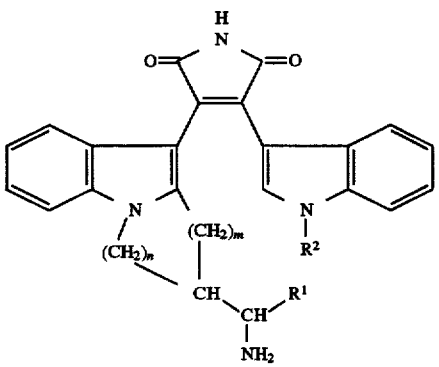

wherein $R^1$ is lower alkyl, lower cycloalkyl, aryl or lower aralkyl;

$R^2$ is hydrogen, aryl or lower alkyl optionally substituted by hydroxy, acyloxy, amino, mono(lower alkyl)amino, di(lower alkyl)amino, carboxy, lower alkoxycarbonyl or aminocarbonyl; and m and n are, independently, the numerals 1 or 2, and pharmaceutically acceptable salts of acidic compounds of formula I with bases and of basic compounds of formula I with acids.

Objects of the invention are the compounds of formula I and their salts and as therapeutically active substances; a process for the preparation of the compounds of formula I and their salts, as well as intermediates useful in said process; medicaments containing the compounds of formula I and their salts and the preparation of these medicaments; and the use of the compounds of formula I and their salt in the control or prevention of illnesses, particularly, in the control or prevention of inflammatory, immunological, oncological, bronchopulmonary, dermatological and cardiovascular disorders, in the treatment of asthma, AIDS or diabetic complications or for the stimulation of hair growth, or for the manufacture of a medicament against inflammatory, immunological, oncological, bronchopulmonary, dermatological and cardiovascular disorders or against asthma, AIDS or diabetic complications or for the stimulation of hair growth.

As used herein, the term "lower alkyl", alone or in combination, denotes unsubstituted straight-chain or branched-chain alkyl group containing 1–6 carbon atoms, such as, methyl, ethyl, propyl, isopropyl, butyl, sec.butyl, tert.butyl, pentyl and the like. The term "lower alkoxy", alone or in combination, denotes an alkyl group, as defined earlier, which is attached via an oxygen atom, exemplary of alkoxy groups are methoxy, ethoxy, propoxy, isopropoxy, butoxy, tert.butoxy and the like. The term "lower cycloalkyl" denotes a cycloalkyl group containing 3–6 carbon atoms, such as, cyclopropyl, cyclobutyl, cyclopentyl and cyclohexyl. The term "aryl" denotes unsubstituted phenyl or phenyl substituted by one or more substituents selected from, for example, halogen, lower alkyl and lower alkoxy, such as, p-chlorophenyl, p-tolyl and p-methoxyphenyl. The term "lower aralkyl" denotes a lower alkyl group, as hereinbefore defined, in which one hydrogen atom has been replaced by an aryl group as hereinbefore defined, such as, benzyl, 2-phenylethyl, p-chlorobenzyl, p-methylbenzyl and p-methoxybenzyl. The term "acyloxy" denotes an acyloxy group derived from an alkanoic acid containing up to 6 carbon atoms, for example, acetoxy, propionyloxy or butyryloxy, or from an aromatic carboxylic acid which can be optionally substituted by halogen, lower alkyl and/or lower alkoxy, such as, benzoyloxy, p-chlorobenzoyloxy, p-toluoyloxy and p-methoxybenzoyloxy. The term "halogen" denotes fluorine, chlorine, bromine or iodine.

The compounds of formula I contain two chiral carbon atoms and can therefore be present in racemic or optically active forms. The invention includes within its scope not only the racemic compounds, but also the optically active isomers.

In the compounds of formula I, $R^1$ preferably is lower alkyl, preferably, lower alkyl containing 1–3 carbon atoms. $R^2$ preferably is lower alkyl, preferably, methyl. Preferably, m is 1 and n is 2.

Particularly preferred compounds of formula I are:

3-[8(S)-[1(R or S)-Aminopropyl]-6,7,8,9-tetrahydropyrido[1,2-a]indol-10-yl]-4-(1-methyl-3-indolyl)-1H-pyrrole-2,5-dione; and 3-[8(S)-[1(S)-amino-2-methylpropyl]-6,7,8,9-tetrahydropyrido-[1,2-a]indol-10-yl]-4-(1-methyl-3-indolyl)-1H-pyrrole-2,5-dione.

Other preferred compounds of formula I are:

3-[8(R or S)-1(R or S)-Aminoethyl]-6,7,8,9-tetrahydropyrido[1,2-a]indol-10-yl]-4-(1-methyl-3-indolyl)-1H-pyrrole-2,5-dione;

3-[8(R or S)-1(R or S)-aminopropyl]-6,7,8,9-tetrahydropyrido[1,2-a]indol-10-yl]-4-(1-methyl-3-indolyl)-1H-pyrrole-2,5-dione;

3-[8(R or S)-1(R or S)-aminobutyl]-6,7,8,9-tetrahydropyrido[1,2-a]indol-10-yl]-4-(1-methyl-3-indolyl)-1H-pyrrole-2,5-dione; and 3-[8(R or S)-1(R or S)-amino-2-methylpropyl]-6,7,8,9-tetrahydropyrido[1,2-a]indol-10-yl]-4-(1-methyl-3-indolyl)-1H-pyrrole-2,5-dione.

The following are also preferred compounds falling under formula I:

3-[8(S)-1(R)-Amino-2-methylpropyl]-6,7,8,9-tetrahydropyrido[1,2-a]indol-10-yl]-4-(1-methyl-3-indolyl)-1H-pyrrole-2,5-dione;

3-[8(R or S)-[alpha (R or S)-aminobenzyl]-6,7,8,9-tetrahydropyrido[1,2-a]indol-10-yl]-4-(1-methyl-3-indolyl)-1H-pyrrole-2,5-dione;

3-[8(S)-[(R or S)-(amino)(cyclopentyl)methyl-6,7,8,9-tetrahydropyrido[1,2-a]indol-10-yl]-4-(1-methyl-3-indolyl)-1H-pyrrole-2,5-dione;

3-[2(R or S)-[1(R or S)-amino-2-methylpropyl]-2,3-dihydro-1H-pyrrolo[1,2-a]indol-9-yl]-4-(1-methyl-3-indolyl)-1H-pyrrole-2,5-dione;

3-[8(RS)-[1(RS)-amino-2-methylpropyl]-7,8,9,10-tetrahydro-6H-azepino[1,2-a]indol-11-yl]-4-(1-methyl-3-indolyl)-1H-pyrrole-2,5-dione;

3-[7(RS)-[1(RS)-amino-2-methylpropyl]-6,7,8,9-tetrahydropyrido[1,2-a]indol-9-yl]-4-(1-methyl-3-indolyl)-1H-pyrrole-2,5-dione; and 3-[8(S)-[1(S)-amino-2-methylpropyl]-6,7,8,9-tetrahydropyrido[1,2-a]indol-10-yl]-4-(1-phenyl-3-indolyl)-1H-pyrrole-2,5-dione.

According to the process provided by the invention, the compounds of formula I, as well as pharmaceutically acceptable salts of acidic compounds of formula I with bases and of basic compounds of formula I with acids can be prepared by cleaving the protecting group denoted by $R^3$ from a compound of the formula

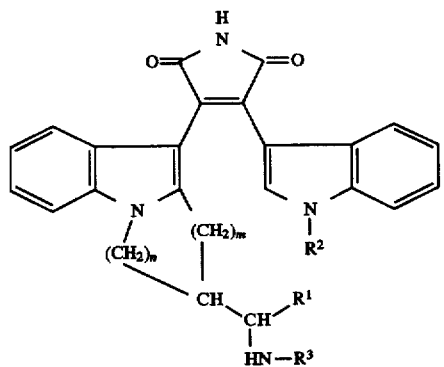

II wherein $R^1$, $R^2$, m and n have the significance given earlier and $R^3$ is a urethane protecting group, and, if desired, functionally modifying a reactive substituent present in $R^2$ in an obtained compound of formula I and, also if desired, converting an acidic compound of formula I into a pharmaceutically acceptable salt with a base or converting a basic compound of formula I into a pharmaceutically acceptable salt with an acid.

The urethane protecting group denoted by $R^3$ in formula II, preferably, is lower alkoxycarbonyl, preferably tert.butoxycarbonyl, or lower aralkoxycarbonyl, preferably, benzyloxycarbonyl.

The cleavage of the protecting group denoted by $R^3$ from a compound of formula II can be carried out in a known manner. For example, when $R^3$ is lower alkoxycarbonyl, the cleavage can be carried out using a mineral acid, such as hydrochloric acid, in an inert organic solvent such as, a cyclic ether, for example, tetrahydrofuran or dioxan, an alkanol, for example, methanol or ethanol, esters, such as, ethyl acetate or a halogenated, particularly, chlorinated hydrocarbon, for example, dichloromethane, or using trifluoroacetic acid. When $R^3$ is an aralkoxy-carbonyl group, the cleavage is carried out by hydrogenolysis in a known manner; for example, using hydrogen in the presence of a catalyst, such as, palladium/charcoal.

The functional modification of a reactive substituent present in $R^2$ in an obtained compound of formula I can comprise the esterification of a carboxy group to a lower alkoxycarbonyl group, the hydrolysis of an acyloxy group to a hydroxy group or the conversion of a lower alkoxycarbonyl group into a carboxy group. All of these modifications can be carried out according to known methods.

The conversion of an acidic compound of formula I into a pharmaceutically acceptable salt can be carried out by treatment with a suitable base in a known manner. Suitable salts are those derived not only from inorganic bases, such as, for example, sodium salts, potassium salts, calcium salts and the like; but also from organic bases, for example, ethylenediamine, monoethanolamine, diethanolamine and like salts. The conversion of a basic compound of formula I into a pharmaceutically acceptable salt can be carried out by treatment with suitable acid in a known manner. Suitable salts are those derived, not only from inorganic acids, for example, hydrochlorides, hydrobromides, phosphates, sulfates and the like, but also from organic acids, for example acetates, citrates, fumarates, tartrates, maleates, methanesulfonates, p-toluenesulfonates and the like.

The starting materials of formula II are novel and also form a part of the invention. They can be prepared, for example, by:

(a) reacting a compound of the formula

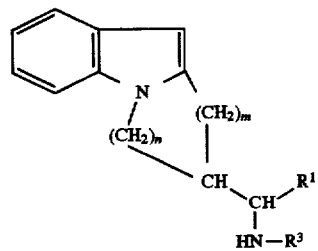

III wherein $R^1$, $R^3$, m and n have the significance given earlier, with oxalyl chloride, condensing the resulting activated glyoxylate of the formula

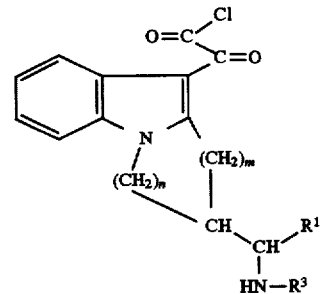

IV wherein $R^1$, $R^3$, m and n have the significance given earlier, with an imidate of the formula

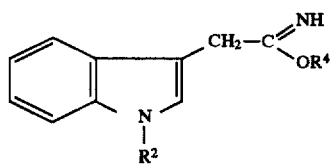

V wherein $R^2$ has the significance given earlier and $R^4$ is lower alkyl, in the presence of a strong base and hydrolyzing and dehydrating the resulting hydroxy-pyrrolinone of the formula

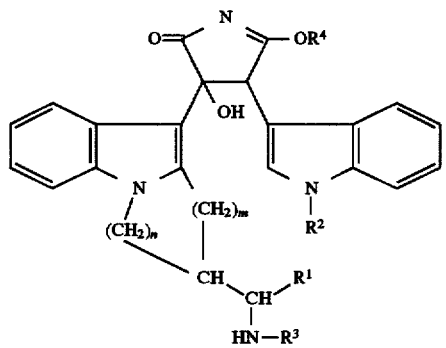

VI wherein $R^1$, $R^2$, $R^3$, $R^4$, m and n have the significance given earlier, or (b) reacting an activated glyoxylate of formula IV with an indolylacetic acid of the formula

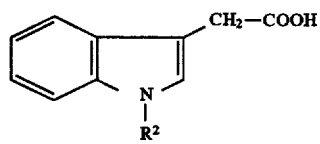

VII wherein $R^2$ has the significance given earlier, in the presence of a strong base and converting the resulting substituted furandione of the formula

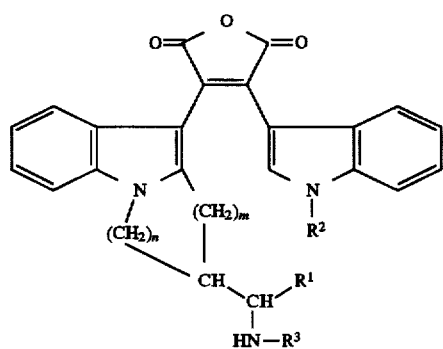

VIII wherein $R^1$, $R^2$, $R^3$, m and n have the significance given earlier, into the corresponding imide starting material of formula II.

The reaction of a compound of formula III with oxalyl chloride is conveniently carried out in the presence of an inert organic solvent, for example, a halogenated aliphatic hydrocarbon, such as, dichloromethane. It is also convenient to carry out this reaction at about 0° C.

The condensation of an activated glyoxylate of formula IV with an imidate of formula V, which is a known compound or an analogue of a known compound, is conveniently carried out in an inert organic solvent. Suitable bases are, for example, tertiary amines, such as, trimethylamine, diisopropylethylamine, 4-dimethylaminopyridine, N-ethylmorpholine and 1,4-diazabicyclo[2.2.2]octane as well as pyridine. Suitable solvents are, for example, halogenated aliphatic hydrocarbons, such as, dichloromethane and chloroform; optionally halogenated aromatic hydrocarbons, such as, benzene, toluene and chlorobenzene; open-chain and cyclic ethers, such as, dimethoxyethane, tert.butyl methyl ether and tetrahydrofurane; formamides, such as, dimethylformamide; esters, such as, ethyl acetate; and nitriles, such as, acetonitrile. The condensation is preferably carried out at a temperature in the range of about 0°C. to 40° C., preferably at room temperature. Further, it is preferred to carry out this condensation in situ.

The hydrolysis and dehydration of a hydroxy-pyrrolinone of formula VI to give a compound of formula II is expediently carried out by treatment with a mineral acid, such as, hydrochloric acid or sulfuric acid or an organic acid, such as methanesulfonic acid or p-toluenesulfonic acid, or by treatment with an acylating reagent, such as, trifluoroacetic anhydride and a suitable base, such as, pyridine, conveniently at about room temperature. The hydroxypyrrolinone of formula VI is preferably hydrolyzed and dehydrated in situ.

The reaction of an activated glyoxylate of formula IV with an indolylacetic acid of formula VII, which is a known compound or an analogue of a known compound, is conveniently carried out in a manner analogous to that described earlier in connection with the condensation of an activated glyoxylate of formula IV with an imidate of formula V.

The conversion of a substituted furandione of formula VIII into a desired imide starting material of formula II can be carried out conveniently by treatment with hexamethyldisilazane in the presence of an alkanol, such as, methanol, in an inert organic solvent. Suitable solvents are, for example, halogenated aliphatic hydrocarbons, such as, dichloromethane and chloroform; optionally halogenated aromatic hydrocarbons, such as, benzene, toluene and chlorobenzene; open-chain and cyclic ethers, such as, dimethoxyethane, tert.butyl methyl ether and tetrahydrofuran; or formamides, such as, dimethylformamide. The reaction is preferably carried out at about room temperature to 100° C., preferably at about 50° C.

The compounds of formula III can be prepared, for example, as illustrated in Reaction Scheme I, in which $R^1$, m and n have the significance given earlier.

REACTION SCHEME I

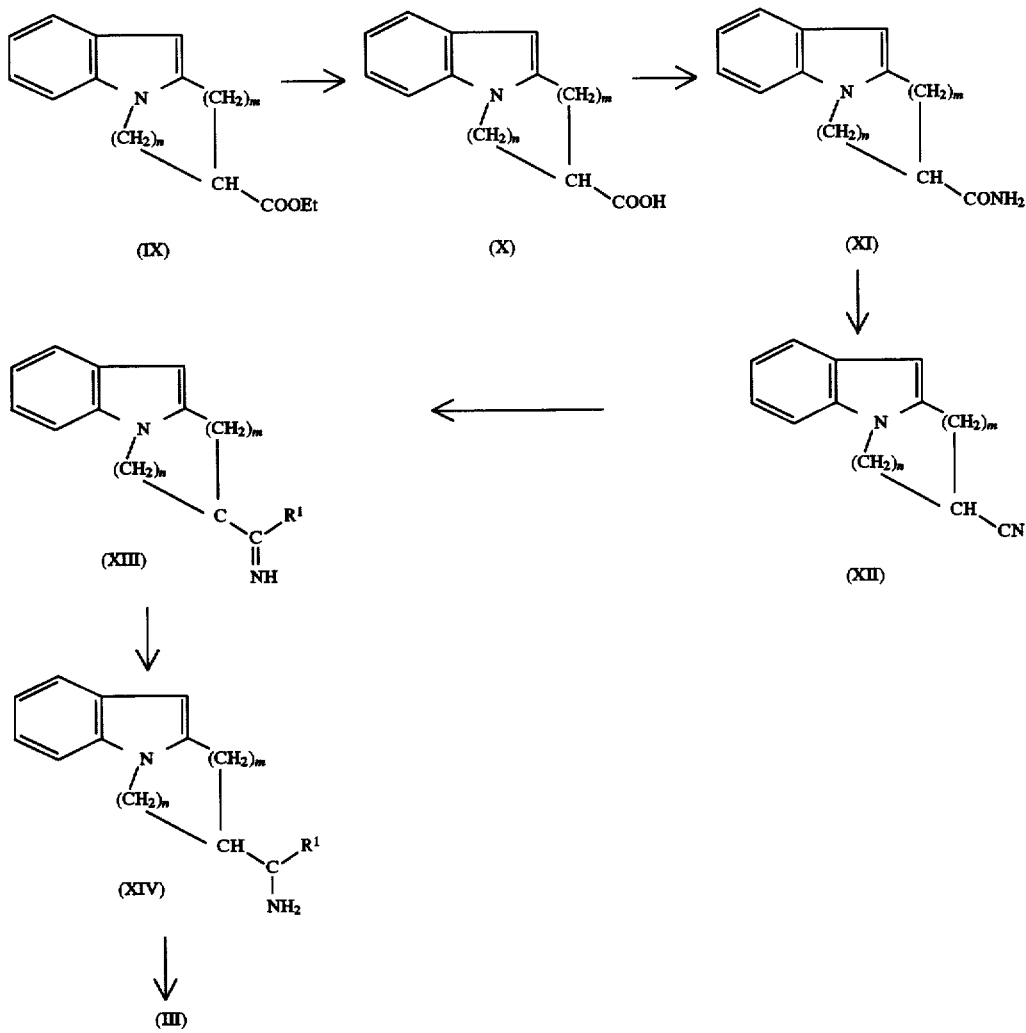

In regard to Reaction Scheme I, all of the individual steps thereof can be carried out according to conventional methods. In the first step, an ethyl ester of formula IX, which is a known compound or an analogue of a known compound, is saponified to the corresponding acid of formula X using, for example, sodium hydroxide solution. The resulting acid is then amidated, for example, by reaction with ethyl chloroformate in the presence of triethylamine followed by treatment with ammonia, and the resulting amide of formula XI is converted into the nitrile of formula XII using, for example, trifluoroacetic anhydride. Therefore, the nitrile of formula XII is reacted with a Grignard reagent of the formula $R^1$—Mg—X, wherein $R^1$ has the significance given earlier and X is halogen, preferably chlorine, and the resulting imine of formula XIII is reduced using a complex metal hydride, for example, lithium aluminum hydride, to a primary amine of formula XIV. This reduction is preferably carried out in situ. The primary amine of formula XIV is converted into a compound of formula III by, for example, reaction with a chloroformate of the formula $R^3Cl$ or an anhydride of the formula $R^3OR^3$, wherein $R^3$ has the significance given earlier, in the presence of a base, such as, triethyl-amine.

Homochiral compounds of formula III, denoted hereinafter as IIIA, can be prepared, for example, as illustrated in the following Reaction Scheme II in which $R^1$, m and n have the significance given earlier and $R^5$ is lower alkyl.

REACTION SCHEME II

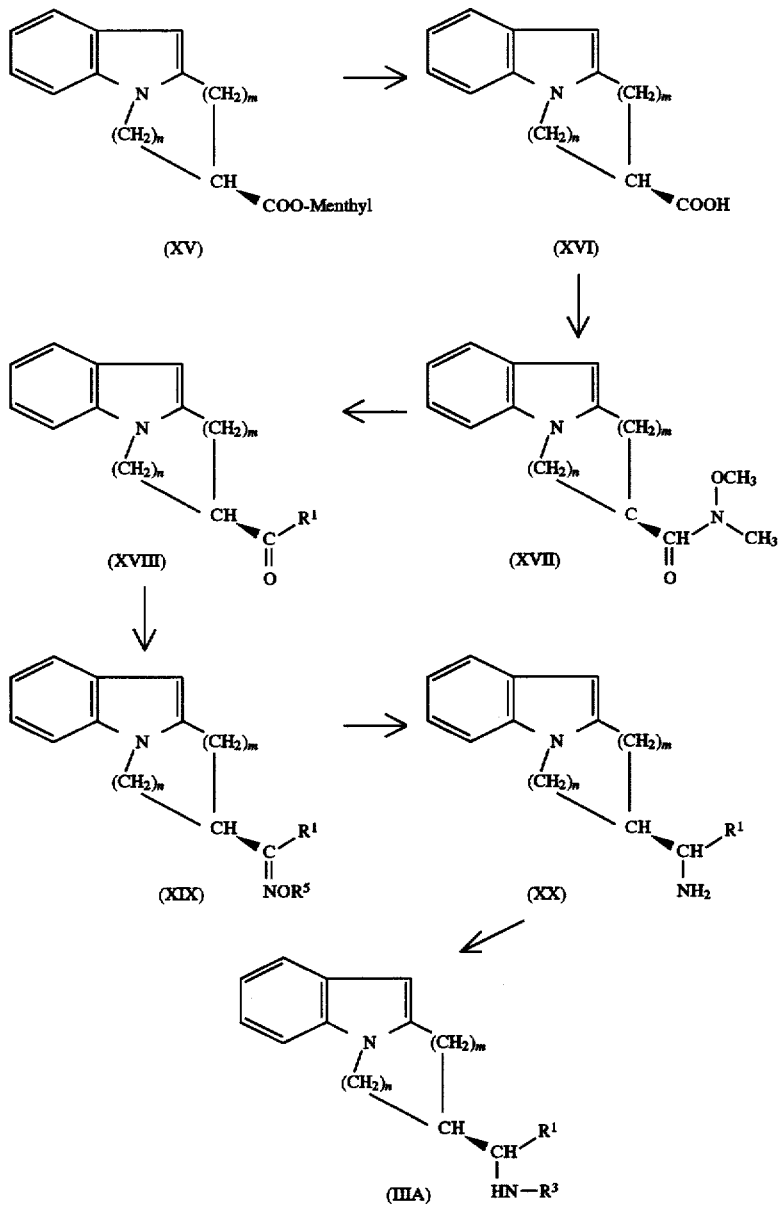

The individual steps of the synthesis, illustrated in Reaction Scheme II, can all be carried out according to known methods. In the first step, a methyl ester of formula XV, which is a known compound or an analogue of a known compound, is converted with a strong acid, for example, concentrated sulfuric acid, into the corresponding carboxylic acid of formula XVI. This acid is then condensed with N,O-dimethylhydroxylamine and the N-methoxy-N-methyl carboxamide of formula XVII obtained is reacted with a Grignard reagent of the formula $R^1$—Mg—X, wherein $R^1$ has the significance given earlier and X is halogen, preferably chlorine, to give a ketone of formula XVIII. Reaction of this ketone with a hydroxylamine of the formula $H_2N$—$OR^5$, wherein $R^5$ has the significance given earlier, gives an oxime of formula XIX which is reduced with a complex metal hydride, such as, lithium aluminum hydride to a primary amine of formula XX. The latter is subsequently converted into a homochiral starting material of formula IIIA by acylation in an analogous manner to that described in Reaction Scheme I for the conversion of a compound of formula XIV into a compound of formula III.

Reaction Scheme III illustrates an alternative route to homochiral starting materials of formula IIIA. In this Reaction Scheme, $R^1$, m and n have the significance given earlier and Ms is methanesulfonyl.

REACTION SCHEME III

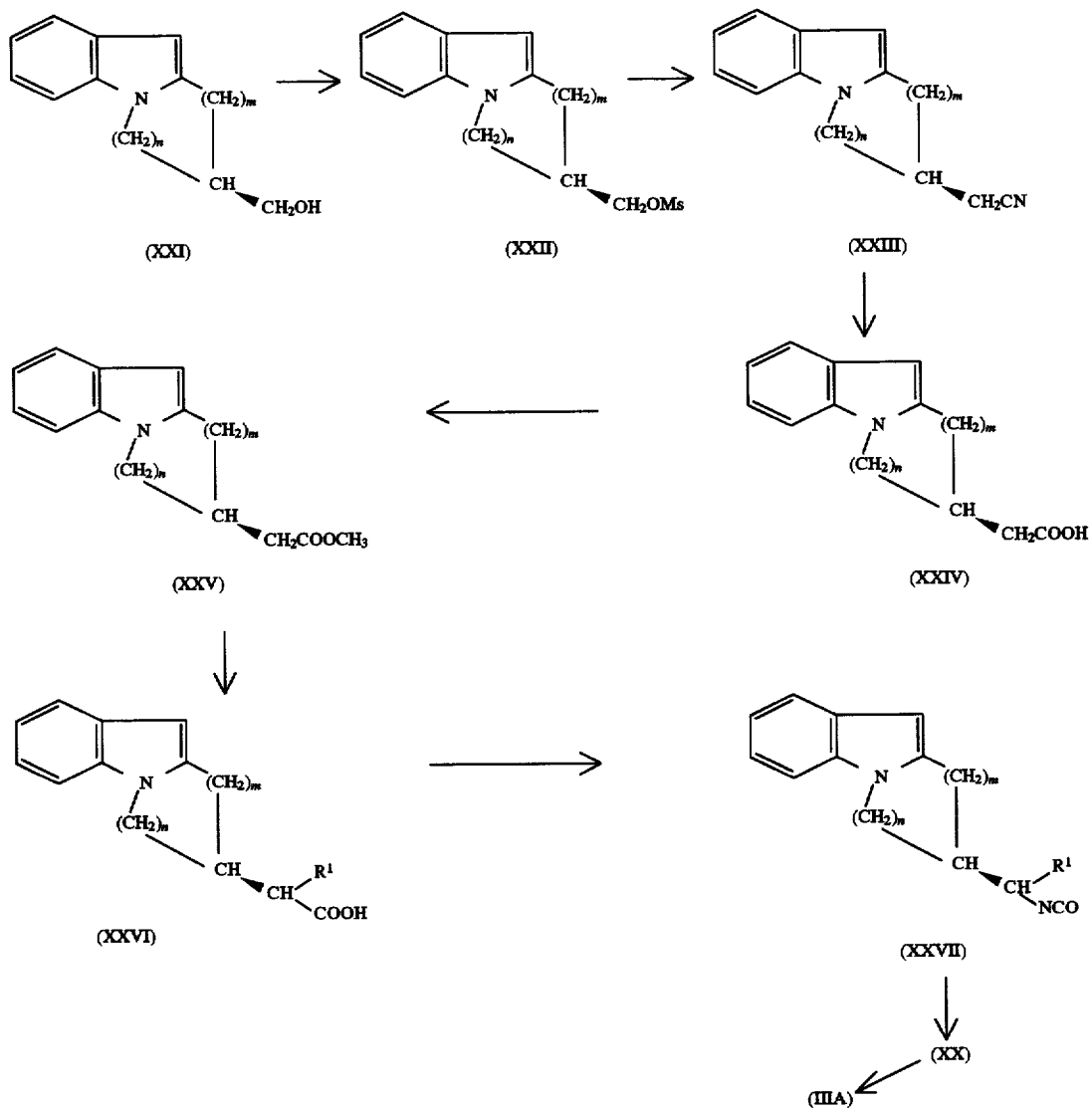

In regard to Reaction Scheme III, all of the individual steps therein can be carried out in a conventional manner. More particularly, an alcohol of formula XXI is sulfonated, for example, with methanesulfonic anhydride, and the methanesulfonate of formula XXII obtained is converted with sodium cyanide into the nitrile of formula XXIII. The latter is hydrolyzed, for example, using sodium hydroxide solution, to the corresponding carboxylic acid of formula XXIV, which is methylated, for example, using methanol in the presence of concentrated sulfuric acid, to the methyl ester of formula XXV. Reaction of a compound of formula XXV with a halide of the formula $R^1$—X, wherein $R^1$ and X have the significance given earlier, in the presence of a strong base, such as, lithium diisopropylamide followed by treatment with sodium hydroxide solution yields the carboxylic acid of formula XXVI. The latter is reacted with diphenylphosphoryl azide to give the isocyanate of formula XXVII which is converted into a primary amine of formula XX by treatment with hydrochloric acid. The conversion of a primary amine of formula XX into a homochiral compound of formula IIIA is carried out by acylation in an analogous manner to that described in connection with Reaction Scheme I.

The compounds of formula I and their pharmaceutically acceptable salts are protein kinase inhibitor. More particularly, the compounds of formula I inhibit cellular processes, for example, cell proliferation and secretion, and can be used in the control or prevention of illnesses, for example, in the control or prevention of inflammatory disorders, such as, arthritis, immune diseases, psoriasis, contact dermatitis, in conjunction with organ transplants and also in oncology. The compounds of formula I inhibit infection of cells with human immunodeficiency virus or Epstein-Barr virus and are thus useful in the treatment of AIDS and infectious mononucleosis. The compounds of formula I and their salts also inhibit smooth muscle contraction and can therefore be used against cardiovascular and bronchopulmonary disorders. Further, they are also useful in asthma therapy. The compounds and salts referred to above also inhibit platelet aggregation and can be used in the control or prevention of thrombosis. Further, they inhibit the release of mediators from activated neutrophils and can therefore be used to control ischaemic damage, for example, in the heart or brain. Again, they inhibit neurotoxicity induced by elevated glucose levels and are thus useful for the treatment of diabetic complications. Finally, the compounds of formula I and their salts stimulate hair growth and can therefore be used to prevent or repress baldness.

The activity of the compounds of formula I and their salts in inhibiting protein kinase C can be demonstrated by means of the test procedure described hereinafter.

The assay system described by Takai et al., BBRC 19, 1218, (1979) can be used. Reaction mixtures (100 μl) contain 10 μM [γ-$^{32}$P]ATP, 0.2 mg/ml (about 15 μM) lysine-rich histone, 0.5 mM $CaCl_2$ and 40 μg/ml phosphatidylserine in 25 mM Tris HCl, 5 mM $MgNO_3$ (pH 7.5) buffer are utilized. The enzyme protein kinase C is isolated from rat brains according to the method of Kikkawa et al., J. Biol. Chem. 257, 13341 (1982).

The reaction is started by adding the enzyme protein kinase C to the reaction mixture, is run at 30° C. for 10 minutes and is then stopped using 1 ml of ice-cold 10% trichloroacetic acid. Acid-precipitable protein is collected on glass fiber discs by filtration. The discs are then washed with 5% trichloroacetic acid containing 20 mM sodium pyrophosphate (in order to remove unreacted ATP), followed by ethanol. The discs are dried and counted. Counts associated with each disc are used as a measure of the incorporation of $^{32}$P from [γ-$^{32}$P]ATP into histone. The degree of enzyme blockade, at each test compound concentration, is calculated from $$\frac{\text{Cpm incorporated + test compound + enzyme}}{\text{Cpm incorporated - test compound + enzyme}} \times 100\%$$

The $IC_{50}$ value is that concentration of test compound which reduces by 50% the protein kinase-induced incorporation of the $^{32}$P under the assay conditions described above.

The results obtaining in the above test with representative compounds of formula I are given in the following Table.

TABLE

| Product of Example No. | $IC_{50}$ (nM) |
|---|---|
| 10 | 3.3 |
| 11 | 5.5 |

The compounds of formula I and their salts can be used as medicaments, for example, in the form of pharmaceutical preparations. The pharmaceutical preparations can be administered orally, for example, in the form of tablets, coated tablets, dragees, hard and soft gelatine capsules, solutions, emulsions or suspensions. However, the pharmaceutical preparations can also be administered rectally, for example in the form of suppositories, or parenterally, for example, in the form of injection solutions.

For the manufacture of pharmaceutical preparations, the compounds of formula I and their salts can be formulated with therapeutically inert, inorganic or organic carriers. Lactose, maize starch or derivatives thereof, talc, stearic acid or its salts and the like can be used, as carriers, for example, for tablets, coated tablets, dragees and hard gelatine capsules. Suitable carriers for soft gelatine capsules are, for example, vegetable oils, waxes, fats, semi-solid and liquid polyols and the like. Depending on the nature of the active substance, no carriers are, however, generally required in the case of soft gelatine capsules. Suitable carriers for the preparation of solutions and syrups are, for example, water, polyols, saccharose, invert sugar, glucose and the like. Suitable carriers for injection solutions are, for example, water, alcohols, polyols, glycerine, vegetable oils and the like. Suitable carriers for suppositories are, for example, natural or hardened oils, waxes, fats, semi-liquid polyols and the like.

The pharmaceutical preparations can also contain preservatives, solubilizing agents, stabilizing agents, wetting agents, emulsifying agents, sweetening agents, coloring agents, flavoring agents, salts for varying the osmotic pressure, buffers, coating agents or antioxidants. The pharmaceutical preparations can also contain still other therapeutically valuable substances. Medicaments containing a compound of formula I or a salt thereof and a therapeutically inert carrier as well as a process for the preparation of such medicaments are also from part of the invention. Such process comprises bringing a compound of formula I or a salt thereof into a galenical administration form together with a therapeutically inert carrier material and, if desired, one or more other therapeutically active substances.

As mentioned above, the compounds of formula I and their salts can be used in the control or prevention of illnesses, especially in the control or prevention of inflammatory, immunological, bronchopulmonary, dermatological and cardiovascular disorders, for the treatment of asthma, AIDS or diabetic complications or for the stimulation of hair growth. The dosage can vary within wide limits and will, of course, be adjusted to the individual requirements in each particular case. In general, in the case of oral administration to adults, a daily dosage of about 5 mg to about 500 mg should be appropriate, although the upper limit may be exceeded when this is found to be expedient. The daily dosage can be administered as a single dose or in divided doses.

The Examples which follow further illustrate the invention:

EXAMPLE 1

A solution of 1.25 g (2.32 mmol) of 3-[8(R or S)-[1(R or S)-tertbutoxyformamidoethyl]-6,7,8,9-tetrahydropyrido[1,2-a]indol-10-yl]-4-(1-methyl-3-indolyl)-1H-pyrrole-2,5-dione (diastereomer A) in 10 ml of ethyl acetate was treated with 30 ml of a saturated solution of hydrogen chloride in ethyl acetate and stirred at room temperature for 18 hours. The solid obtained was removed by filtration and dried to give 1.0 g of 3-[8(R or S)-[1(R or S)-aminoethyl]-6,7,8,9-tetrahydropyrido[1,2-a]indol-10-yl]-4-(1-methyl-3-indolyl)-1H-pyrrole-2,5-dione hydrochloride (diastereomer A) as a red solid of melting point 324°–325° C.

The 3-[8(R or S)-[1(R or S)-tert-butoxyformamidoethyl]-6,7,8,9-tetrahydropyrido[1,2-a]indol-10-yl]-4-(1-methyl-3-indolyl)-1H-pyrrole-2,5-dione (diastereomer A) used as the starting material was prepared as follows:

(i) A stirred suspension of 27 g (126 mmol) of 6,7,8,9-tetrahydropyrido[1,2-a]indole-8-carboxylic acid in 30 ml of water and 450 ml of acetone was cooled to 0° C. and treated in succession with 14.7 g (145 mmol) of triethylamine and 17.3 g (159 mmol) of ethyl chloroformate. After 0.5 hour, 6.3 ml of 0.880 ammonia was added and stirring was continued for 1 hour. The solvent was removed under reduced pressure and the residue was triturated with aqueous ethanol. The product was filtered off and dried to give 13 g of 6,7,8,9-tetrahydropyrido[1,2-a]indole-8-carboxamide, as a white solid of melting point 165°–168° C.

(ii) 25.7 g (126 mmol) of trifluoroacetic anhydride were added dropwise to a stirred suspension of 26.5 g (123 mmol) of 6,7,8,9-tetrahydropyrido[1,2-a]indole-8-carboxamide and 23.4 g (300 mmol) of pyridine in 500 ml of dry dioxane at 10° C. After completion of the addition, the solvent was removed under reduced pressure and the residue was crystallized from methanol to give 13 g of 6,7,8,9-tetrahydropyrido[1,2-a]indole-8(RS)-carbonitrile, as a light tan solid of melting point 106°–109° C.

(iii) A solution of 1.4 g (7.2 mmol) of 6,7,8,9-tetrahydropyrido[1,2-a]indole-8(RS)-carbonitrile in 400 ml of dry toluene was treated with 7 ml (21 mmol) of 3M solution of methylmagnesium chloride in tetrahydrofuran and the solution obtained was heated to reflux under nitrogen for 0.5 hour. The solution was then added to 17 ml (17 mmol) of a 1M solution of lithium aluminum hydride in tetrahydrofuran. The solution obtained was heated to reflux for 15 minutes, cooled and treated dropwise with about 20 ml of water. The precipitate was filtered off and washed with 100 ml of ethyl acetate and the combined filtrate and washings were evaporated under reduced pressure to give 1.55 g of a light brown oil.

The oil was dissolved in 70 ml of dry dichloromethane and treated with 1.5 g (15 mmol) of triethylamine followed by 1.8 g (7.4 mmol) of di-tert.butyl dicarbonate at 0° C. under nitrogen. The stirred solution was allowed to warm to room temperature and stirring was continued for 1 hour. The solvent was removed under reduced pressure and the product was purified by flash chromatography on silica gel using diethyl ether/petroleum ether (1:2) for the elution to give 925 mg of tert.butyl [1(R or S)-(6,7,8,9-tetrahydropyrido[1,2-a]indol-8(R or S)-yl)ethyl]carbamate, as a mixture of diastereomers in the form of a white solid of melting point 114°–117° C.

(iv) A stirred solution of 3.0 g (9.57 mmol) of tert.butyl [1(R or S)-(6,7,8,9-tetrahydropyrido[1,2-a]indol-8(R or S)-yl)ethyl]carbamate in 150 ml of dichloromethane was treated dropwise at 0° C. with 1.28 g (10.3 mmol) of oxalyl chloride. After 5 minutes, the solvent was removed under reduced pressure and the residue was dissolved in 150 ml of dichloromethane and treated with 2.94 g (11 mmol) of isopropyl 1-methyl-3-indoleacetimidate hydrochloride and 4.38 g (43 mmol) of triethylamine at 0° C. under nitrogen. After warming to room temperature, the solution was stirred for 24 hours, washed with water and dried over magnesium sulfate. The solvent was removed by evaporation and the residue was dissolved in 30 ml of pyridine. The resulting solution was cooled to ice bath temperature and treated dropwise with 1.5 ml (10.8 mmol) of trifluoroacetic anhydride. After 15 minutes, the solvent was removed under reduced pressure and the residue was partitioned between 200 ml of ethyl acetate and 200 ml of 0.2M hydrochloric acid. The organic layer was washed with 50 ml of sodium bicarbonate solution, dried over magnesium sulfate and evaporated to dryness. The residue was purified by flash chromatography on silica gel using ethyl acetate/petroleum ether (1:2) for the elution to give 1.35 g of 3-[8(R or S)-[1(R or S)-tert.butoxyformamidoethyl]-6,7,8,9-tetrahydropyrido[1,2-a]indol-10-yl]-4-(1-methyl-3-indolyl)-1H-pyrrole-2,5-dione (diastereomer A) in the form of a red solid of melting point 255°–7° C. Further elution gave 1.38 g of diastereomer B as a red solid of melting point 230°–233° C.

EXAMPLE 2

In an analogous manner to that described in the first paragraph of Example 1, from 1.38 g of 3-[8(R or S)-[1(R or S)-tert.butoxyformamidoethyl]-6,7,8,9-tetrahydropyrido[1,2-a]indol-10-yl]-4-(1-methyl-3-indolyl)-1H-pyrrole-2,5-dione (diastereomer B), prepared as described in Example 1(iv), there were obtained 930 mg of 3-[8(R or S)-[1(R or S)-aminoethyl]-6,7,8,9-tetrahydropyrido[1,2-a]indol-10-yl]-4-(1-methyl-3-indolyl)-1H-pyrrole-2,5-dione hydrochloride (diastereomer B) as a red solid of melting point 254°–258° C.

EXAMPLE 3

In a manner analogous to that described in the first paragraph of Example 1, from 180 mg of 3-[8(R or S)-[1(R or S)-tert.butoxyformamidopropyl]-6,7,8,9-tetrahydropyrido[1,2-a]indol-10-yl]-4-(1-methyl-3-indolyl)-1H-pyrrole-2,5-dione (diastereomer A) there were obtained 115 mg of 3-[8(R or S)-[1(R or S)-aminopropyl]-6,7,8,9-tetrahydropyrido[1,2-a]indol-10-yl]-4-(1-methyl-3-indolyl)-1H-pyrrole-2,5-dione hydrochloride (diastereomer A) as a red solid of melting point 321°–323°C.

The 3-[8(R or S)-[1(R or S)-tert.butoxyformamidopropyl]-6,7,8,9-tetrahydropyrido[1,2-a]indol-10-yl]-4-(1-methyl-3-indolyl)-1H-pyrrole-2,5-dione (diastereomer A) used as the starting material was prepared as follows:

(i) In a manner analogous to that described in Example 1(iii), from 500 mg (2.5 mmol) of 6,7,8,9-tetrahydropyrido[1,2-a]indole-8(RS)-carbonitrile and 2.5 ml (5 mmol) of a 2M solution of ethylmagnesium bromide in tetrahydrofuran, there were obtained 480 mg of tert.butyl [1(R or S)-(6,7,8,9-tetrahydropyrido[1,2-a]indol-8(R or S)-yl)propyl]carbamate, as a mixture of diastereomers in the form of a white solid of melting point 153°–156° C.

(ii) In a manner analogous to that described in Example 1(iv), from 440 mg (1.34 mmol) of tert.butyl [1(R or S)-(6,7,8,9-tetrahydropyrido[1,2-a]indol-8(R or S)-yl)propyl]carbamate, there were obtained 180 mg of 3-[8(R or S)-[1(R or S)-tert.butoxyformamidopropyl]-6,7,8,9-tetrahydropyrido[1,2-a]indol-10-yl]-4-(1-methyl-3-indolyl)-1H-pyrrole-2,5-dione (diastereomer A) as a red gum. Further elution gave 130 mg of diastereomer B as a red gum.

EXAMPLE 4

In a manner analogous to that described in the first paragraph of Example 1, from 130 mg of 3-[8(R or S)-1(R or S)-tert.butoxyformamidopropyl]-6,7,8,9-tetrahydropyrido[1,2-a]indol-10-yl]-4-(1-methyl-3-indolyl)-1H-pyrrole-2,5-dione [diastereomer B, prepared as described in Example 3(ii)], there were obtained 65 mg of 3-[8(R or S)-[1(R or S)-aminopropyl]-6,7,8,9-tetrahydropyrido[1,2-a]indol-10-yl]-4-(1-methyl-3-indolyl)-1H-pyrrole-2,5-dione hydrochloride (diastereomer B) as a red solid of melting point 245°–249° C.

EXAMPLE 5

In a manner analogous to that described in the first paragraph of Example 1, from 400 mg (0.7 mmol) of 3-[8-(R or S)-[1(R or S)-tert.butoxyformamidobutyl]-6,7,8,9-tetrahydropyrido[1,2-a]indol-10-yl]-4-(1-methyl-3-indolyl)-1H-pyrrole-2,5-dione (diastereomer A), there were obtained 310 mg of 3-[8(R or S)-[1(R or S)-aminobutyl]-6,7,8,9-tetrahydropyrido[1,2-a]indol-10-yl]-4-(1-methyl-3-indolyl)-1H-pyrrole-2,5-dione hydrochloride (diastereomer A) as a red solid of melting point 237°–241°C.

The 3-[8-(R or S)-[1(R or S)-tert.butoxyformamidobutyl]-6,7,8,9-tetrahydropyrido[1,2-a]indol-10-yl]-4-(1-methyl-3- indolyl)-1H-pyrrole-2,5-dione (diastereomer A) used as the starting material was prepared as follows:

In a manner analogous to that described in Example 1(iii) and (iv), from 1.0 g (5 mmol) of 6,7,8,9-tetrahydropyrido [1,2-a]indole-8(RS)-carbonitrile and 5.0 ml (10 mmol) of a 2M solution of n-propyl-magnesium chloride in diethyl ether, there were obtained 470 mg of 3-[8(R or S)-[1(R or S)-tert.butoxyformamidobutyl]-6,7,8,9-tetrahydropyrido[1,2-a]indol-10-yl]-4-(1-methyl-3-indolyl)-1H-pyrrole-2,5-dione (diastereomer A) as a red solid of melting point 227°–9° C. Further elution gave 285 mg of diastereomer B as a red solid of melting point 169°–172°C.

EXAMPLE 6

In a manner analogous to that described in the first paragraph of Example 1, from 270 mg (0.48 mmol) of 3-[8(R or S)-1(R or S)-tert.butoxyformamidobutyl]-6,7,8,9-tetrahydropyrido[1,2-a]indol- 10-yl]-4-(1-methyl-3-indolyl)-1H-pyrrole-2,5-dione (diastereomer B), prepared as described in the second paragraph of Example 5, there were obtained 210 mg of 3-[8(R or S)-[1(R or S)-aminobutyl]-6,7,8,9-tetrahydropyrido[1,2-a]indol-10-yl]-4-(1-methyl-3-indolyl)-1H-pyrrole-2,5-dione hydrochloride (diastereomer B) as a red solid of melting point 235°–238° C.

EXAMPLE 7

In a manner analogous to that described in the first paragraph of Example 1, from 400 mg (0.7 mmol) of 3-[8(R or S)-[1(R or S)-tert.butoxyformamido- 2-methylpropyl]-6,7,8,9-tetrahydropyrido-[1,2-a]indol-10-yl]-4-(1-methyl-3-indolyl)-1H-pyrrole-2,5-dione (diastereomer A), there were obtained 300 mg of 3-[8(R or S)-[1(R or S)-amino-2-methylpropyl]-6,7,8,9-tetrahydropyrido[1,2-a]indol-10-yl]-4-(1-methyl-3-indolyl)-1H-pyrrole-2,5-dione hydrochloride (diastereomer A) as a red solid of melting point 254°–256° C.

The 3-[8(R or S)-[1(R or S)-tert.butoxyformamido-2-methylpropyl]-6,7,8,9-tetrahydropyrido[1,2-a]indol-10-yl]-4-(1-methyl-3-indolyl)-1H-pyrrole-2,5-dione (diastereomer A) used as the starting material was prepared as follows:

(i) A solution of 2.0 g (10 mmol) of 6,7,8,9-tetrahydropyrido[1,2-a]indole-8(RS)-carbonitrile in 150 ml of dry toluene was treated with 10 ml (20 mmol) of a 2M solution of isopropylmagnesium chloride in tetrahydrofuran and the solution obtained was heated to reflux for 20 minutes. The solution was cooled and treated dropwise with 24 ml (24 mmol) of a 1M solution of lithium aluminum hydride in tetrahydrofuran. The solution obtained was stirred at room temperature for 1.5 hours, cooled and treated dropwise with about 20 ml of water. The precipitate was filtered off, washed with 100 ml of dichloromethane and the combined filtrates were evaporated under reduced pressure to give 7.2 g of pale brown oil. The oil was dissolved in 100 ml of dry dichloromethane and treated with 2.34 g (23.4 mmol) of triethylamine followed by 2.8 g (11.6 mmol) of di-tert.-butyldicarbonate at 0° C. under nitrogen. The stirred solution was allowed to warm to room temperature and stirring was continued for 70 hours. The solvent was removed under reduced pressure and the products were purified by flash chromatography on silica gel using diethyl ether/petroleum ether (1:2) for the elution to give 800 mg of tert.butyl [1(R or S)-[6,7,8,9-tetrahydropyrido[1,2-a]indol-8(R or S)-yl]-2-methylpropyl]carbamate (diastereomer A) as a white solid of melting point 118°–9° C. Further elution gave 420 mg of diastereomer B as a white solid of melting point 128°–129° C.

(ii) A stirred solution of 770 mg (2.25 mmol) of tert.butyl [1(R or S)-[6,7,8,9-tetrahydropyrido[1,2-a]indol-8(R or S)-yl]-2-methylpropyl]carbamate (diastereomer A) in 30 ml of dichloromethane at 0° C. was treated dropwise with 287 mg (2.4 mmol) of oxalyl chloride. After 5 minutes, the solvent was removed under reduced pressure and the residue was dissolved in 30 ml of dichloromethane and treated with 686 mg (2.57 mmol) of isopropyl 1-methyl-3-indoleacetimidate hydrochloride and 1.02 g (10 mmol) of triethylamine at 0° C. under nitrogen. After warming to room temperature, the solution was stirred for 18 hours, washed with 50 ml of water and dried over magnesium sulfate. The solvent was removed by evaporation and the residue was dissolved in 10 ml of pyridine. The stirred solution was cooled to ice bath temperature and treated dropwise with 664 µl (4.8 mmol) of trifluoroacetic anhydride. After 15 minutes, 50 ml of ethyl acetate was added and the organic phase was washed with water and 2M hydrochloric acid, dried over magnesium sulfate and evaporated to dryness. The residue was purified by flash chromatography on silica gel using ethyl acetate/petroleum ether (1:2) for the elution to give 460 mg of 3-[8(R or S)-[1(R or S)-tert.butoxyformamido-2-methylpropyl]-6,7,8,9-tetrahydropyrido[1,2-a]indol-10-yl]-4-(1-methyl-3-indolyl)-1H-pyrrole-2,5-dione (diastereomer A) as a red solid of melting point 223°–224° C.

EXAMPLE 8

In an analogous manner to that described in the first paragraph of Example 1, from 270 mg (0.48 mmol) of 3-[8(R or S)-[1(R or S)-tert.butoxyformamido-2-methylpropyl]-6,7,8,9-tetrahydropyrido[1,2-a]indol-10-yl]-4-(1-methyl-3-indolyl)-1H-pyrrole-2,5-dione (diastereomer B), there were obtained 180 mg of 3-[8(R or S)-[1(R or S)-amino-2-methylpropyl]-6,7,8,9-tetrahydropyrido[1,2-a]indol-10-yl]-4-9-(1-methyl-3-indolyl)-1H-pyrrole-2,5-dione hydrochloride (diastereomer B) as a red solid of melting point 248°–250° C.

The 3-[8(R or S)-[1(R or S)-tert.butoxyformamido-2-methylpropyl]-6,7,8,9-tetrahydropyrido[1,2-a]indol-10-yl]-4-(1-methyl-3-indolyl)-1H-pyrrole-2,5-dione (diastereomer B) used as the starting material was prepared as follows:

In an analogous manner to that described in Example 7(ii), from 385 mg of tert.butyl [1(R or S)-[6,7,8,9-tetrahydropyrido[1,2-a]indol-8(R or S)-yl]-2-methylpropyl]carbamate (diastereomer B), prepared as described in Example 7(i), there were obtained 270 mg of 3-[8(R or S)-[1(R or S)-tert.butoxyformamido-2-methylpropyl]-6,7,8,9-tetrahydropyrido[1,2-a]indol-10-yl]-4-(1-methyl-3-indolyl)-1H-pyrrole-2,5-dione (diastereomer B) as a red gum.

EXAMPLE 9

In a manner analogous to that described in the first paragraph of Example 1, from 1.2 g (2.17 mmol) of 3-[8(S)-[1(R or S)-tert.butoxyformamidopropyl]-6,7,8,9-tetrahydropyrido[1,2-a]indol-10-yl]-4-(1-methyl-3-indolyl)-1H-pyrrole-2,5-dione (diastereomer A), there were obtained 850 mg of 3-[8(S)-[1(R or S)-aminopropyl]-6,7,8,9-tetrahydro-pyrido[1,2-a]indol-10-yl]-4-(1-methyl-3-indolyl)-1H-pyrrole-2,5-dione hydrochloride (diastereomer A) as a red solid of melting point 304°–308° C.

The 3-[8(S)-[1(R or S)-tert.butoxyformamidopropyl]-6,7, 8,9-tetrahydropyrido[1,2-a]indol-10-yl]-4-(1-methyl-3-indolyl)-1H-pyrrole-2,5-dione (diastereomer A) used as the starting material was prepared as follows:

(i) An ice-cooled solution of 50.0 g (248 mmol) of 8(S)-hydroxymethyl-6,7,8,9-tetrahydropyrido[1,2-a]indole in 500 ml of dichloromethane was treated with 50 ml (358 mmol) of triethylamine and 52.0 g (298 mmol) of methanesulfonic anhydride over a period of 20 minutes. After 2 hours, 250 ml of water were added and the organic phase was washed in succession with two 250 ml portions of saturated sodium bicarbonate solution and 200 ml of water. The organic phase was then dried over magnesium sulfate and evaporated. The residual solid was triturated with ether, filtered off and dried in vacuo to give 65.4 g of [6,7,8,9-tetrahydropyrido[1,2-a]indol-8(S)-yl]-methyl methanesulfonate as a pale pink solid of melting point 114°–5° C.; $[\alpha]_D^{20} = -39.7°$ (c=1%, $CH_2Cl_2$).

(ii) 18.0 g (367 mmol) of sodium cyanide were added to a solution of 65.0 g (233 mmol) of (6,7,8,9-tetrahydropyrido[1,2-a]indol-8(S)-yl)methyl methanesulfonate in 500 ml of dimethylformamide and the mixture was heated at 70° C. for 24 hours. The mixture was partitioned between 1000 ml of water and 600 ml of ethyl acetate. The aqueous phase was extracted twice with 700 ml of ethyl acetate each time and the combined extracts were washed in twice with 500 ml of water each time, dried over magnesium sulfate and evaporated. The brown solid obtained was dissolved in ethyl acetate and the solution was filtered through a pad of silica gel. The solvent was removed in a vacuum and the residue was crystallized from methanol to give 25.8 g of 6,7,8,9-tetrahydropyrido[1,2-a]indole-8(S)-acetonitrile as a light brown solid of melting point 100°–101° C.; $[\alpha]_D^{20}$ –40.6° (c=0.84%, $CH_2Cl_2$).

(iii) A solution of 27.0 g (129 mmol) of 6,7,8,9-tetrahydropyrido[1,2-a]indole-8(S)-acetonitrile and 120 ml of 2M sodium hydroxide in 400 ml of 1,2-ethanediol was heated to reflux for 4 hours. 400 ml of ethyl acetate were added and the organic phase was washed in succession with 500 ml of water, 150 ml of 2M hydrochloric acid and three 500 ml portions of water, dried over magnesium sulfate and evaporated to give 29 g of [8(S)-(6,7,8,9-tetrahydropyrido[1,2-a]indolyl]acetic acid as a pale pink solid of melting point 118°–120° C.

(iv) A solution of 29 g (127 mmol) of 8(S)-(6,7,8,9-tetrahydropyrido[1,2-a]indolyl)acetic acid and 5 ml of concentrated sulfuric acid in 500 ml of methanol was heated to reflux for 1 hour. The mixture was concentrated under reduced pressure and the product was filtered off and dried to give 28.4 g of methyl [8(S)-(6,7,8,9-tetrahydropyrido[1,2-a]indolyl]acetate as a pale pink solid of melting point 84°–87° C.

(v) 10 g (100 mmol) of diisopropylamine in 60 ml of dry tetrahydrofuran were treated at 0° C. under nitrogen with 63 ml (100 mmol) of a 1.6M solution of n-butyllithium in hexane and stirred for 15 minutes. The solution obtained was cooled to −78° C. and a solution of 14.9 g (61.3 mmol) of methyl [8(S)-6,7,8,9-tetrahydropyrido[1,2-a]indolyl]acetate in 60 ml of tetrahydrofuran was added dropwise. After 30 minutes, 15.6 g (100 mmol) of ethyl iodide were added and the mixture was stirred for 0.5 hour. A further 8 g of ethyl iodide were then added and the mixture was allowed to warm to room temperature for about 1 hour. The mixture was partitioned between 300 ml of diethyl ether and 20 ml of 2M hydrochloric acid. The organic phase was washed three times with 300 ml of water each time, dried over magnesium sulfate and evaporated to give 17 g of a pale orange oil. A sample was crystallized from methanol to give methyl alpha (R or S)-ethyl-6,7,8,9-tetrahydropyrido[1,2-a]indole-8(S)-acetate (diastereomers A+B) as a pale pink solid of melting point 87°–90° C.

(vi) A solution of 17 g (63 mmol) of methyl alpha (R or S)-ethyl-6,7,8,9-tetrahydropyrido[1,2-a]indole-8(S)-acetate (diastereomers A+B) in 150 ml of methanol was treated with 130 ml of 2M sodium hydroxide and heated to reflux for 18 hours. The cooled solution was added to 150 ml of 4M hydrochloric acid and the resulting precipitate was filtered off and partitioned between 200 ml of dichloromethane and 100 ml of water. The organic phase was separated, dried over magnesium sulfate and evaporated to give 15 g of alpha (R or S)-6,7,8,9-tetrahydropyrido[1,2-a]indole-8(S)-acetic acid (diastereomers A+B) as a pale pink solid.

(vii) A stirred solution of 15 g (58.4 mmol) of alpha (R or S)-6,7,8,9-tetrahydropyrido[1,2-a]indole-8(S)-acetic acid (diastereomers A+B) in 450 ml of toluene was treated with 6.5 g (65 mmol) of triethylamine and 18.6 g (67.5 mmol) of diphenylphosphonyl azide at room temperature under nitrogen. After 1 hour at room temperature, the mixture was heated to reflux for 0.5 hour, cooled and the solvent was removed under reduced pressure. The residue was purified by flash chromatography on silica gel using diethyl ether/petroleum ether (1:3) for the elution to give 14 g of the isocyanate as a colorless oil. The oil was dissolved in 400 ml of dioxan and 150 ml of 2M hydrochloric acid and the solution obtained was stirred at room temperature for 18 hours. The solution was concentrated and partitioned between 300 ml of ethyl acetate and 2M sodium hydroxide solution. The aqueous layer was extracted with 100 ml of ethyl acetate and the combined organic solutions were washed twice with 400 ml of water each time, dried over magnesium sulfate and evaporated to dryness to give 7.7 g of a cream colored foam.

This foam in 200 ml of dry dichloromethane was treated with 7.6 g (75 mmol) of triethylamine and 10.9 g (50 mmol) of di-tert.butyl dicarbonate and the mixture was stirred at room temperature for 3 hours. The solvent was removed under reduced pressure and the residue was subjected to flash chromatography on silica gel using diethyl ether/petroleum ether (1:2) for the elution to give 4.5 g of tert.butyl [1(R or S)-[6,7,8,9-tetrahydropyrido[1,2-a]indole-8(S)-yl]propyl] carbamate (diasteroisomers A+B) as a white solid of melting point 152°–158° C.

(viii) In a manner analogous to that described in Example 1(iv), from 4.3 g (13.1 mmol) of tert.butyl [1(R or S)-[6,7,8,9-tetrahydropyrido-[1,2-a]indol-8(S)-yl]propyl]carbamate (diastereomers A+B), there were obtained 1.2 g of 3-[8(S)-[1(R or S)-tert.butoxyformamidopropyl]-6,7,8,9-tetrahydropyrido[1,2-a]indol-10-yl]-4-(1-methyl-3-indolyl)-1H-pyrrole-2,5-dione (diastereomer A) and 2.0 g of diastereomer B, both as red solids.

EXAMPLE 10

In a manner analogous to that described in the first paragraph of Example 1, from 2.0 g (3.62 mmol) of 3-[8

(S)-[1(R or S)-tert.butoxyformamidopropyl]-6,7,8,9-tetrahydro-pyrido[1,2-a]indol-10-yl]-4-(1-methyl-3-indolyl)-1H-pyrrole-2,5-dione (diastereomer B), prepared as described in Example 9, there were obtained 1.28 g of 3-[8(S)-[1(R or S)-aminopropyl]-6,7,8,9-tetrahydropyrido [1,2-a]indol-10-yl]-4-(1-methyl-3-indolyl)-1H-pyrrole-2,5-dione hydrochloride (diastereomer B) as a red solid of melting point 247°–253° C.

EXAMPLE 11

In a manner analogous to that described in the first paragraph of Example 1, from 1.46 g of 3-[8(S)-[1(S)-tert.butoxyformamido-2-methylpropyl]-6,7,8,9-tetrahydropyrido[1,2-a]indol-10-yl]-4-(1-methyl-3-indolyl)-1H-pyrrole-2,5-dione, there were obtained 1.29 g of 3-[8 (S)-[1(S)-amino-2-methylpropyl]-6,7,8,9-tetrahydropyrido [1,2-a]indol-10-yl-4-(1-methyl-3-indolyl)-1H-pyrrole-2,5-dione hydrochloride as a red solid of melting point 253°–256° C.

The 3-[8(S)-[1(S)-tert.butoxyformamido-2-methylpropyl]-6,7,8,9-tetrahydropyrido[1,2-a]indol-10-yl]-4-(1-methyl-3-indolyl)-1H-pyrrole-2,5-dione used as the starting material was prepared as follows:

(i) To 40 g (114 mmol) of 6,7,8,9-tetrahydropyrido[1,2-a]indole-8(S)-carboxylic acid 1-menthyl ester were added 50 ml of concentrated sulfuric acid and the mixture obtained was stirred until all starting material had dissolved (about 20 minutes). The solution was poured carefully into 1500 ml of ice-water and the resulting precipitate was filtered off, washed with petroleum ether/toluene (3:1) and dried to give 24.2 g of 6,7,8,9-tetrahydropyrido[1,2-a]indole-8(S)-carboxylic acid as a white solid of melting point 251°–253° C.

(ii) A stirred suspension of 24.0 g (111 mmol) of 6,7,8,9-tetrahydropyrido[1,2-a]indole-8(S)-carboxylic acid in 500 ml of dichloromethane was treated in succession at 0° C. with 24 ml (138 mmol) of diisopropylethylamine, 13.24 g (136 mmol) of N,O-dimethylhydroxylamine hydro-chloride, 10 mg of dimethylaminopyridine and 23.04 g (112 mmol) of dicyclohexylcarbodiimide. The mixture obtained was stirred at room temperature for 18 hours and filtered, and the solid was washed twice with 100 ml of dichloromethane each time. The combined filtrates were evaporated to dryness and the residue was purified by flash chromatography on silica gel using ethyl acetate/petroleum ether (1:3) for the elution to give 22.6 g of a white solid. A sample was triturated with ether/petroleum ether to give 6,7,8,9-tetrahydro-N-methoxy-N-methyl-pyrido[1,2-a]indole-8(S)-carboxamide as a white solid of melting point 78°–80° C.

(iii) A stirred solution of 10.0 g (38.7 mmol) of 6,7,8,9-tetrahydro-N-methoxy-N-methyl-pyrido[1,2-a]indole-8(S)-carboxamide in 250 ml of tetrahydrofuran was treated dropwise at 0° C. with 60 ml (120 mmol) of a 2M solution of isopropylmagnesium chloride in tetrahydrofuran. The mixture was stirred at room temperature for 18 hours and poured into 250 ml of saturated ammonium chloride solution. The aqueous phase was washed four times with 100 ml of diethyl ether each time and the combined ethereal extracts were washed with 200 ml of brine, dried over magnesium sulfate and evaporated to dryness. The product was purified by flash chromatography on silica gel using ethyl acetate/petroleum ether (1:3) for the elution to give 4.4 g of isopropyl 6,7,8,9-tetrahydropyrido[1,2-a]indol-8(S)-yl ketone as a white solid of melting point 78°–79° C.

(iv) A suspension of 4.0 g (16.6 mmol) of isopropyl 6,7,8,9-tetrahydropyrido[1,2-a]indol-8(S)-yl ketone in 120 ml of ethanol was treated with a solution of 2.30 g (33 mmol) of hydroxylamine hydrochloride and 1.0 g (25 mmol) of sodium hydroxide in 20 ml of water. The mixture obtained was heated to reflux for 3.5 hour, cooled and filtered. The solid obtained was dried to give 3.54 g of oxime as a white solid.

The oxime was dissolved in 150 ml of dry tetrahydrofuran and treated with 12.5 ml (12.5 mmol) of a 1M solution of lithium aluminum hydride in tetrahydrofuran. The solution obtained was heated to reflux for 3 hours under nitrogen, cooled and cautiously treated with 150 ml of water. The mixture was extracted with 200 ml of ethyl acetate and then with two 150 ml portions of ethyl acetate, and the combined organic extracts were dried over magnesium sulfate and evaporated to dryness. The residue was dissolved in 150 ml of dichloromethane and the solution obtained was treated with 3 ml (21.5 mmol) of triethylamine and 3.4 g (15.6 mmol) of di-tert.butyl dicarbonate and stirred for 18 hours. The mixture was washed with 150 ml of saturated ammonium chloride solution, dried over magnesium sulfate and evaporated under reduced pressure. Purification by flash chromatography on silica gel using diethyl ether/petroleum ether (1:3) for the elution gave 1.4 g of tert.butyl [1(R)-(6,7,8,9-tetrahydropyrido [1,2-a]indol-8(S)-yl)-2-methylpropyl]carbamate as a white solid of melting point 122°–124° C. Further elution gave 1.1 g of tert.butyl [1(S)-[6,7,8,9-tetrahydropyrido[1,2-a]indol-8(S)-yl]-2-methylpropyl] carbamate as a white solid of melting point 154°–155° C.

(v) In a manner analogous to that described in Example 1(iv), from 1.1 g of tert.butyl [1(S)-[6,7,8,9-tetrahydropyrido[1,2-a]indol-8(S)-yl]-2-methylpropyl] carbamate, there were obtained 1.46 g of 3-[8(S)-[1(S) -tert.butoxyformamido-2-methylpropyl]-6,7,8,9-tetrahydropyrido[1,2-a]indol-10-yl]-4-(1-methyl-3-indolyl)-1H-pyrrole-2,5-dione as a red foam.

EXAMPLE 12

In a manner analogous to that described in the first paragraph of Example 1, from 0.5 g (0.88 mmol) of 3-[8 (S)-[1(R)-tert.butoxyformamido-2-methylpropyl]-6,7,8,9-tetrahydropyrido[1,2-a]indol-10-yl]-4-(1-methyl-3-indolyl)-1H-pyrrole-2,5-dione, there was obtained 0.41 g of 3-[8(S)-[1(R)-amino-2-methylpropyl]-6,7,8,9-tetrahydropyrido[1,2-a]indol-10-yl]-4-(1-methyl-3-indolyl)-1H-pyrrole-2,5-dione hydrochloride as a red solid of melting point 235–242.

The 3-[8(S)-[1(R)-tert.butoxyformamido-2-methylpropyl]-6,7,8,9-tetrahydropyrido[1,2-a]indol-10-yl]-4-(1-methyl-3-indolyl)-1H-pyrrole-2,5-dione used as the starting material was prepared as follows:

In a manner analogous to that described in Example 1(iv), from 0.94 g of tert.butyl [1(R)-[6,7,8,9-tetrahydropyrido[1,2-a]indol-8(S)-yl]-2-methylpropyl]carbamate, prepared as described in Example 11(i)–(iv), there were obtained 1.05 g of 3-[8(S)-[1(R)-tert.butoxyformamido-2-methylpropyl]-6,7,8,9-tetrahydropyrido[1,2-a]indol-10-yl]-4-(1-methyl-3-indolyl)-1H-pyrrole-2,5-dione as a red foam.

EXAMPLE 13

In a manner analogous to that described in the first paragraph of Example 1, from 100 mg of 3-[8(R or S)-[alpha (R or S)-tert.butoxyformamidobenzyl]-6,7,8,9-tetrahydropyrido[1,2-a]-indol-10-yl]-4-(1-methyl-3-indolyl)-1H-pyrrole-2,5-dione (diastereomer A), there were obtained 50 mg of 3-[8(R or S) [alpha (R or S)-aminobenzyl]-6,7,8,9-tetrahydropyrido[1,2-a]indol-10-yl]-4-(1-methyl-3-indolyl)-1H-pyrrole-2,5-dione hydrochloride (diastereomer A) as a red solid of melting point 234°–237° C.

The 3-[8(R or S) [alpha(R or S)-tert.butoxyformamidobenzyl]-6,7,8,9-tetrahydropyrido[1,2-a]-indol-10-yl]-4-(1-methyl-3-indolyl)-1H-pyrrole-2,5-dione (diastereomer A) used as the starting material was prepared as follows:

(i) In a manner analogous to that described in Example 1(iii), from 1.0 g (5.1 mmol) of 6,7,8,9-tetrahydropyrido[1,2-a]indole-8(RS)-carbonitrile and 3.7 ml (11 mmol) of a 3M solution of phenylmagnesium bromide in tetrahydrofuran, there was obtained 0.9 g of tert.butyl [alpha (R or S)-(6,7,8,9-tetrahydropyrido[1,2-a]indol-8(R or S)-yl)benzyl] carbamate as a mixture of diastereomers in the form of a white solid of melting point 160°–165° C.

(ii) In a manner analogous to that described in Example 1(iv), from 800 mg (2.1 mmol) of tert.butyl [alpha (R or S)-(6,7,8,9-tetrahydropyrido[1,2-a]indol-8-(R or S)-yl)benzyl]carbamate, there were obtained 330 mg of 3-[8(R or S)-[alpha (R or S)-tert.butoxyformamidobenzyl]-6,7,8,9-tetrahydropyrido[1,2-a]-indol-10-yl]-4-(1-methyl-3-indolyl)-1H-pyrrole-2,5-dione (diastereomer A) as a red gum. Further elution gave 280 mg of diastereomer B as a red gum.

EXAMPLE 14

In a manner analogous to that described in the first paragraph of Example 1, from 200 mg of 3-[8(R or S)-[alpha (R or S)-tert.butoxyformamidobenzyl]-6,7,8,9-tetrahydropyrido[1,2-a]indol-10-yl]-4-(1-methyl-3-indolyl)-1H-pyrrole-2,5-dione (diastereomer B), prepared as described in Example 13(ii), there were obtained 70 mg of 3-[8(R or S)-[alpha (R or S)-aminobenzyl]-6,7,8,9-tetrahydropyrido[1,2-a]-indol-10-yl]-4-(1-methyl-3-indolyl)-1H-pyrrole-2,5-dione hydrochloride (diastereomer B) as a red solid of melting point 226°–233° C.

EXAMPLE 15

In a manner analogous to that described in the first paragraph of Example 1, from 200 mg of 3-[8(S)-[(R or S)-(tert.butoxyformamido) (cyclopentyl)methyl]-6,7,8,9-tetrahydropyrido[1,2-a]indol-10-yl]-4-(1-methyl-3-indolyl)-1H-pyrrole-2,5-dione (diastereomer A), there were obtained 150 mg of 3-[8(S)-[(R or S)-(amino)(cyclopentyl)methyl]-6,7,8,9-tetrahydropyrido[1,2-a]indol-10-yl]-4-(1-methyl-3-indolyl)-1H-pyrrole-2,5-dione hydrochloride (diastereomer A) as a red solid of melting point 236°–241° C.

The 3-[8(S)-[(R or S)-(tert.butoxyformamido)(cyclopentyl)-methyl]-6,7,8,9-tetrahydropyrido[1,2-a]indol-10-yl]-4-(1-methyl-3-indolyl)-1H-pyrrole-2,5-dione used as the starting material was prepared as follows:

(i) In a manner analogous to that described in Example 11(iii), from 2.0 g (7.75 mmol) of 6,7,8,9-tetrahydro-N-methoxy-N-methylpyrido[1,2-a]indole-8(S)-carboxamide and 15 ml (30 mmol) of a 2M solution of cyclopentylmagnesium chloride in diethyl ether, there were obtained 1.1 g of cyclopentyl 6,7,8,9-tetrahydropyrido[1,2-a]indol-8(S)-yl ketone as a pale yellow solid of melting point 69° C.

(ii) In a manner analogous to that described in Example 11(iv), from 1.05 g (3.9 mmol) of cyclopentyl 6,7,8,9-tetrahydropyrido[1,2-a]indol-8(S)-yl ketone, there were obtained 330 mg of 8(S)-[(R or S)-(tert.butoxyformamido)(cyclopentyl)methyl]-6,7,8,9-tetrahydropyrido[1,2-a]indole (diastereomer A) as a white solid of melting point 140°–143° C. Further elution gave 430 mg of diastereomer B as a white solid of melting point 58°–63° C.

(iii) In a manner analogous to that described in Example 1(iv), from 300 mg of 8(S)-[(R or S)-(tert.butoxyformamido)(cylopentyl)methyl]-6,7,8,9-tetrahydropyrido[1,2-a]indole (diastereomer A), there were obtained 200 mg of 3-[8(S)-[(R or S)-(tert.butoxyformamido)(cyclopentyl)methyl]-6,7,8,9-tetrahydropyrido[1,2-a]indol-10-yl]-4-(1-methyl-3-indolyl)-1H-pyrrole-2,5-dione as a red gum.

EXAMPLE 16

In a manner analogous to that described in the first paragraph of Example 1, from 250 mg of 3-[8(S)-[(R or S)-(tert.butoxyformamido)(cyclopentyl)methyl]-6,7,8,9-tetrahydropyrido[1,2-a]indol-10-yl]-4-(1-methyl-3-indolyl)-1H-pyrrole-2,5-dione (diastereomer B), there were obtained 160 mg of 3-[8(S)-[(R or S)-(amino)(cyclopentyl)methyl]- 6,7,8,9-tetrahydropyrido{1,2-a]indol-10-yl]-4-(1-methyl-3-indolyl)-1H-pyrrole-2,5-dione hydrochloride (diastereomer B) as a red solid of melting point 241°–245° C.

The 3-[8(S)-[(R or S)-(tert.butoxyformamido)(cyclopentyl)methyl]-6,7,8,9-tetrahydropyrido[1,2-a]indol-10-yl]-4-(1-methyl-3-indolyl)-1H-pyrrole-2,5-dione, used as the starting material, was prepared as follows:

In a manner analogous to that described in Example 1(iv), from 400 mg of 8(S)-[(R or S)-(tert.butoxyformamido)(cyclopentyl)methyl]-6,7,8,9-tetrahydropyrido[1,2-a]indole (diastereomer B), prepared as described in Example 15(i)–(ii), there were obtained 250 mg of 3-[8(S)-[(R or S)-(tert.butoxyformamido)(cyclopentyl)methyl]-6,7,8,9-tetrahydropyrido[1,2-a]indol-10-yl]-4-(1-methyl-3-indolyl)-1H-pyrrole-2,5-dione as a red gum.

EXAMPLE 17

In a manner analogous to that described in the first paragraph of Example 1, from 40 mg of 3-[2(R or S)-[1(R or S)-tert.butoxyformamido-2-methylpropyl]-2,3-dihydro-1H-pyrrolo[1,2-a]indol-9-yl]-4-(1-methyl-3-indolyl)-1H-pyrrole-2,5-dione (diastereomer A), there were obtained 20 mg of 3-[2-(R or S)-[1(R or S)-amino-2-methylpropyl]-2,3-dihydro-1H-pyrrolo[1,2-a]indol-9-yl]-4-(1-methyl-3-indolyl)-1H-pyrrole-2,5-dione hydrochloride (diastereomer A) as a red solid of melting point 224°–230° C.

The 3-[2(R or S)-[1(R or S)-tert.butoxyformamido-2-methylpropyl]-2,3-dihydro-1H-pyrrolo[1,2-a]indol-9-yl]-4-(1-methyl-3-indolyl)-1H-pyrrole-2,5-dione used as the starting material was prepared as follows:

(i) A solution of 8.0 g (35 mmol) of ethyl 2,3-dihydro-1H-pyrrolo 1,2-a]indole-2(RS)-carboxylate in 100 ml of ethanol and 100 ml of water was treated with 3.0 g (75 mmol) of sodium hydroxide. The mixture was heated at reflux for 15 minutes, then cooled and acidified with 60 ml (120 mmol) of 2M hydrochloric acid. The suspension was filtered and the solid was washed with 50 ml of water and then dried to give 5.9 g of 2,3-dihydro-1H-pyrrolo[1,2-a]indole-2(RS)-carboxylic acid as a white solid of melting point 171°–173° C.

(ii) In a manner analogous to that described in Example 11(ii), from 4.0 g (20 mmol) of 2,3-dihydro-1H-pyrrolo[1,2-a]indole-2(RS)-carboxylic acid, there were obtained 2.35 g of 2,3-dihydro-N-methoxy-N-methyl-1H-pyrrolo[1,2-a]indole-2(RS)-carboxamide as a white solid of melting point 87°–88° C.

(iii) A suspension of 840 mg (35 mg atom) of magnesium turnings in 60 ml of tetrahydrofuran was treated dropwise with a solution of 4.4 g (37 mmol) of 2-bromopropene in 10 ml of tetrahydrofuran. The mixture was heated at reflux for an additional 30 minutes, then cooled to 0° C. and added at this temperature to a solution of 2.3 g (9.4 mmol) of 2,3-dihydro-N-methoxy-N-methyl-1H-pyrrolo[1,2-a]indole-2(RS)-carboxamide in 50 ml of tetrahydrofuran. After stirring at 0° C. for 30 minutes, the mixture was poured into 200 ml of saturated aqueous ammonium chloride solution. The solution was extracted with 200 ml of ethyl acetate and the organic phase was dried over magnesium sulfate and filtered. Addition of petroleum ether (b.p. 40°–60° C.) gave a precipitate which was filtered off and dried to give 1.6 g of a white solid. The solid was dissolved in 100 ml of ethanol and hydrogenated over 200 mg of 10% palladium-on-carbon at atmospheric pressure for 1 hour. The catalyst was removed by filtration and the filtrate was concentrated under reduced pressure until crystallization commenced. The product was filtered off and dried to give 1.55 g of isopropyl 2,3-dihydro-1H-pyrrolo[1,2-a]indol-2(RS)-yl ketone as a white solid of melting point 104°–105° C.

(iv) In a manner analogous to that described in Example 11(iv), from 1.5 g of isopropyl 2,3-dihydro-1H-pyrrolo[1,2-a]indol-2(RS)-yl-ketone, there were obtained 830 mg of tert.butyl [1(R or S)-[2,3-dihydro-1H-pyrrolo[1,2-a]indol-2(R or S)-yl]-2-methylpropyl]carbamate as a mixture of diastereomers. The mixture was stirred in 20 ml of ethyl acetate saturated with hydrogen chloride for 2 hours. The solid obtained was filtered off and purified by flash chromatography on silica gel using methanol/dichloromethane (1:10) for the elution to give 150 mg of 2(R or S)-[1(R or S)-amino-2-methylpropyl]-2,3-dihydro-1H-pyrrolo[1,2-a]indole hydrochloride (diastereomer A) in the form of a white solid. Further elution gave 150 mg of diastereomer B as a white solid.

(v) A solution of 100 mg (0.38 mmol) of 2(R or S)-[1(R or S)-amino-2-methylpropyl]-2,3-dihydro-1H-pyrrolo[1,2-a]indole hydrochloride (diastereomer A) in 30 ml of dichloromethane was treated with 110 mg (0.5 mmol) of di-tert.butyldicarbonate and 100 mg (1 mmol) of triethylamine and stirred for 72 hours. The solution was washed in succession with 30 ml of 1M hydrochloric acid and 30 ml of saturated aqueous sodium bicarbonate and then dried over magnesium sulfate. After filtration, concentration of the filtrate under reduced pressure and purification of the residue by flash chromatography using diethyl ether/petroleum ether (b.p. 40°–60° C.) (1:2) for the elution gave 100 mg of tert.butyl [1(R or S)-[2,3-dihydro-1H-pyrrolo[1,2-a]indol-2-(R or S)-yl]-2-methylpropyl]carbamate (diastereomer A) in the form of an oil.

(vi) In a manner analogous to that described in the first paragraph of Example 1, from 55 mg of tert.butyl [1(R or S)-[2,3-dihydro-1H-pyrrolo[1,2-a]indol-2-(R or S)-yl]-2-methylpropyl]carbamate (diastereomer A), there were obtained 40 mg of 3-[2(R or S)-[1(R or S)-tert.butoxyformamido-2-methylpropyl]-2,3-dihydro-1H-pyrrolo[1,2-a]indol-9-yl]-4-(1-methyl-3-indolyl)-1H-pyrrole-2,5-dione as a red oil

EXAMPLE 18

In a manner analogous to that described in the first paragraph of Example 1, from 80 mg of 3-[2(R or S)-[1(R or S)-tert.butoxyformamido- 2-methylpropyl]-2,3-dihydro-1H-pyrrolo[1,2-a]indol-9-yl]-4-(1-methyl-3-indolyl)-1H-pyrrole-2,5-dione (diastereomer B), there were obtained 40 mg of 3-[2(R or S)-amino-2-methylpropyl]2,3-dihydro-1H-pyrrolo [1,2-a]indol-9-yl]-4-(1-methyl-3-indolyl)-1H-pyrrole-2,5-dione hydro-chloride (diastereomer B) as a red solid of melting point 220°–225° C.

The 3-[2(R or S)-[1(R or S)-tert.butoxyformamido-2-methylpropyl]-2,3-dihydro-1H-pyrrolo[1,2-a]indol-9-yl]-4-(1-methyl-3-indolyl)-1H-pyrrole-2,5-dione used as the starting material was prepared as follows:

(i) In a manner analogous to that described in Example 17(v), from 90 mg (0.34 mmol) of 2(R or S)-[1-(R or S)-amino-2-methylpropyl]-2,3-dihydro-1H-pyrrolo[1,2-a]indole hydrochloride (diastereomer B), prepared as described in Example 17(iv), there were obtained 100 mg of tert.butyl [1(R or S)-[2,3-dihydro-1H-pyrrolo[1,2-a]indol-2-(R or S)-yl]-2-methylpropyl]carbamate (diastereomer B) as an oil.

(ii) In a manner analogous to that described in Example 1(iv), from 100 mg of tert.butyl [1(R or S)-[2,3-dihydro-1H-pyrrolo[1,2-a]indol-2-(R or S)-yl]-2-methylpropyl]carbamate, there were obtained 80 mg of 3-[2(R or S)-[1(R or S)-tert.butoxyformamido-2-methylpropyl]-2,3-dihydro-1H-pyrrolo[1,2-a]indol-9-yl]-4-(1-methyl-3-indolyl)-1H-pyrrole-2,5-dione as a red oil.

EXAMPLE 19

In a manner analogous to that described in the first paragraph of Example 1, from 320 mg of 3-[8(RS)-[1(RS)-tert.butoxyformamido-2-methylpropyl]-7,8,9,10-tetrahydro-6H-azepino[1,2-a]indol-11-yl]-4-(1-methyl-3-indolyl)-1H-pyrrole-2,5-dione, there were obtained 220 mg of 3-[8(RS)-[1(RS)-amino-2-methylpropyl]-7,8,9,10-tetrahydro-6H-azepino [1,2-a]indol-11-yl]-4-(1-methyl-3-indolyl)-1H-pyrrole-2,5-dione hydro-chloride as a red solid of melting point 248°–256° C.

The 3-[8(RS)-[1(RS)-tert.butoxyformamido-2-methylpropyl]-7,8,9,10-tetrahydro-6H-azepino[1,2-a]indol-11-yl]-4-(1-methyl-3-indolyl)-1H-pyrrole-2,5-dione used as the starting material was prepared as follows:

(i) In a manner analogous to that described in Example 1l(ii), from 1.0 g (4.4 mmol) of 7,8,9,10-tetrahydro-6H-azepino[1,2-a]indole-8(RS)-carboxylic acid, there was obtained 0.8 g of 7,8,9,10-tetrahydro-N-methoxy-N-methyl-6H-azepino[1,2-a]indole-8(RS)-carboxamide as a white solid of melting point 134°–135° C.

(ii) In a manner analogous to that described in Example 17(iii), from 0.8 g (2.9 mmol) of 7,8,9,10-tetrahydro-N-methoxy-N-methyl-6H-azepino[1,2-a]indole-8(RS)-carboxamide, there was obtained 0.56 g of isopropyl 7,8,9,10-tetrahydro-6H-azepino[1,2-a]indol-8(RS)-yl ketone as a white solid of melting point 79°–80° C.

(iii) In a manner analogous to that described in Example 11(iv), from 0.56 g (2.2 mmol) of isopropyl 7,8,9,10-tetrahydro-6H-azepino[1,2-a]indol-8(RS)-yl ketone, there were obtained 330 mg of tert.butyl [1(RS)-[7,8,9,10-tetrahydro-6H-azepino[1,2-a]indol-8(RS)-yl]-2-methyl-propyl]carbamate as a mixture of diastereomers in the form of a white solid of melting point 152°–153° C.

(iv) In a manner analogous to that described in Example 1(iv), from 300 mg tert.butyl [1(RS)-[7,8,9,10-tetrahydro-6H-azepino-[1,2-a]indol-8(RS)-yl]-2-methylpropyl]carbamate, there were obtained 350 mg of 3-[8(RS)-[1(RS)-tert.butoxyformamido-2-methylpropyl]-7,8,9,10-tetrahydro-6H-azepino[1,2-a]indol-11-yl]-4-(1-methyl-3-indolyl)-1H-pyrrole-2,5-dione as a red oil.

EXAMPLE 20

In a manner analogous to that described in the first paragraph of Example 1, from 800 mg of 3-[7(RS)-[1(RS)-tert.butoxyformamido-2-methylpropyl]-6,7,8,9-tetrahydropyrido[1,2-a]indol-10-yl]-4-(1-methyl-3-indolyl)-1H-pyrrole-2,5-dione, there were obtained 480 mg of 3-[7(RS)-[1(RS)-amino-2-methylpropyl]-6,7,8,9-tetrahydropyrido[1,2-a]indol-10-yl]-4-(1-methyl-3-indolyl)-1H-pyrrole-2,5-dione hydro-chloride as a red solid of melting point 238°–244° C.

The 3-[7(RS)-[1(RS)-tert.butoxyformamido-2-methylpropyl]-6,7,8,9-tetrahydropyrido[1,2-a]indol-10-yl]-4-(1-methyl-3-indolyl)-1H-pyrrole-2,5-dione used as the starting material was prepared as follows:

(i) In a manner analogous to that described in Example 11(ii), from 2.0 g (9.3 mmol) of 6,7,8,9-tetrahydropyrido[1,2-a]indole-7(RS)-carboxylic acid, there were obtained 1.6 g of 6,7,8,9-tetrahydro-N-methoxy-N-methyl-pyrido[1,2-a]indole-7(RS)-carboxamide as a pale yellow oil.

(ii) In a manner analogous to that described in Example 17(iii), from 1.6 g of 6,7,8,9-tetrahydro-N-methoxy-N-methyl-pyrido[1,2-a]indole-7(RS)-carboxamide, there were obtained 1.05 g of isopropyl 6,7,8,9-tetrahydropyrido[1,2-a]indol-7(RS)-yl ketone as a tan solid of melting point 43°–44° C.

(iii) In a manner analogous to that described in Example 11(iv), from 1.0 g of isopropyl 6,7,8,9-tetrahydropyrido[1,2-a]indol-7(RS)-yl ketone there were obtained 800 mg of tert.butyl [1(RS)-[6,7,8,9-tetrahydropyrido[1,2-a]indol-7(RS)-yl]-2-methylpropyl]carbamate as a white solid of melting point 55°–57° C. (as a mixture of diastereomers).

(iv) In a manner analogous to that described in Example 1(iv), from 700 mg of tert.butyl [1(RS)-[6,7,8,9-tetrahydropyrido[1,2-a]indol- 7(RS)-yl]-2-methylpropyl]carbamate, there were obtained 800 mg of 3-[7(RS)-[1(RS)-tert.butoxyformamido-2-methylpropyl]-6,7,8,9-tetrahydropyrido [1,2-a]indol-10-yl]-4-(1-methyl-3-indolyl)-1H-pyrrole-2,5-dione as a red gum.

EXAMPLE 21

In a manner analogous to that described in the first paragraph of Example 1, from 1.3 g of 3-[8(S)-[1(S)-tert.butoxyformamido-2-methyl-propyl]-6,7,8,9-tetrahydropyrido[1,2-a]indol-10-yl]-4-(1-phenyl-3-indolyl)-1H-pyrrole-2,5-dione, there were obtained 1.12 g of 3[8(S)-[1(S)-amino-2-methylpropyl]-6,7,8,9-tetrahydropyrido[1,2-a]indol-10-yl]-4-(1-phenyl-3-indolyl)-1H-pyrrole-2,5-dione hydrochloride as a red solid of melting point 235°–245° C.

The 3-[8(S)-[1(S)-tert.butoxyformamido-2-methylpropyl]-6,7,8,9-tetrahydropyrido[1,2-a]indol-10-yl]-4-(1-phenyl-3-indolyl)-1H-pyrrole-2,5-dione used as the starting material was prepared as follows:

(i) An ice-cooled solution of 10 g (51.8 mmol) of 1-phenylindole in 100 ml of anhydrous diethyl ether was treated dropwise during 5 minutes with a solution of 6 ml (68.8 mmol) of oxalyl chloride in 20 ml of anhydrous diethyl ether. The mixture was stirred for 3 hours while cooling with ice and then treated with 25 ml of ethanol in one portion. After stirring for 10 minutes, the solvent was removed under reduced pressure and the residual solid was crystallized from 60 ml of ethanol to give 12.38 g of ethyl 1-phenylindole-3-glyoxylate as a pale yellow solid of melting point 109°–110° C.

(ii) A mixture of 10 g (34.1 mmol) of ethyl 1-phenylindole-3-glyoxylate and about 25 g of Raney nickel in 350 ml of ethanol and 150 ml of water was heated at reflux for 6 hours. The suspension was filtered through glass fiber filter paper and the solid was washed with four 50 ml portions of ethyl acetate while taking care not to allow the solid to dry. The filtrate was concentrated under reduced pressure and the residue was purified by flash chromatography on silica gel using ethyl acetate/hexane (1:2) for the elution. There were obtained 6.38 g of ethyl 1-phenylindole-3-acetate as a yellow oil.

(iii) A solution of 6.3 g (22.6 mmol) of ethyl 1-phenylindole-3-acetate in 20 ml of ethanol was treated with 20 ml (40 mmol) of 2M sodium hydroxide solution and left at room temperature for 17 hours. Ethanol was removed under reduced pressure and the aqueous solution was washed with two 20 ml portions of diethyl ether. The aqueous phase was acidified with concentrated hydrochloric acid and the suspension obtained was stored at 0° C. for 2 hours. The suspension was filtered and the solid was crystallized from methanol/water (2:1) to give 5.6 g 1-phenylindole-3-acetic acid as a blue-grey solid of melting point 131°–135° C.

(iv) An ice-cooled solution of 3 g (8.77 mmol) of tert.butyl [1(S)-[6,7,8,9-tetrahydropyrido[1,2-a]indol-8(S)-yl]-2-methylpropyl]carbamate, prepared as described in Example 11(iv), in 50 ml of anhydrous diethyl ether was treated dropwise under a nitrogen atmosphere over a period of 5 minutes with a solution of 0.85 ml (9.74 mmol) of oxalyl chloride in 5 ml of anhydrous diethyl ether. After an additional 5 minutes, the solvent was removed under reduced pressure and the residue was dissolved in 50 ml of dry dichloromethane. The solution was added dropwise at 0° C. to a stirred mixture of 2.2 g (8.77 mmol) of 1-phenylindole-3-acetic acid and 3.65 ml (26.3 mmol) of triethylamine in 50 ml of dry dichloromethane. The mixture was stirred for 17 hours and then the solvent was removed under reduced pressure. Purification by flash chromatography on silica gel using ethyl acetate/hexane (1:2) for the elution followed by crystallization from ethyl acetate/hexane gave 1.6 g of 3[8(S)-[1(S)-tert.butoxyformamido-2-methylpropyl]-6,7,8,9-tetrahydropyrido[1,2-a]indol-10-yl]-4-(1-phenyl-3- indolyl)-furan-2,5-dione as an orange coloured solid of melting point 148°–150° C.

(v) A solution of 1.6 g (2.54 mmol) of 3[8(S)-[1(S)-tert.butoxy formamido-2-methylpropyl]-6,7,8,9-tetrahydropyrido[1,2-a]indol-10-yl]-4-(1-phenyl-3-indolyl)-furan-2,5-dione in 20 ml of dry N,N-dimethylformamide was treated with 5.35 ml (25.4 mmol) of hexamethyldisilazane and 0.41 g (12.8 mmol) of methanol. The solution was heated at 50° C. for 3 hours and then treated with an additional 5.35 ml (24.8 mmol) of hexamethyldisilazane and 0.41 g (12.8 mmol) of methanol. After a total of 6 hours the solvent was evaporated under reduced pressure and the residue was re-evaporated with 20 ml of methanol. Flash chromatography of the residue on silica gel using ethyl acetate/hexane (1:2) for the elution gave 1.35 g of 3[8(S)-[1(S)-tert.butoxyformamido-2-methylpropyl]-6,7,8,9-tetrahydropyrido[1,2-a]indol-10-yl]-4-(1-phenyl-3-indolyl)-1H-pyrrole-2,5-dione as a red solid of melting point 165°–168° C.

The Examples which follow illustrate typical pharmaceutical preparations containing compounds provided by the invention:

EXAMPLE A

Tablets containing the following ingredients may be produced in a conventional manner:

| Ingredient | Per tablet |
| --- | --- |
| Compound of formula I | 5.0 mg |
| Lactose | 125.0 mg |
| Maize starch | 75.0 mg |
| Talc | 4.0 mg |
| Magnesium stearate | 1.0 mg |
| Tablet weight | 210.0 mg |

EXAMPLE B

Capsules containing the following ingredients may be produced in a conventional manner:

| Ingredient | Per capsule |
| --- | --- |
| Compound of formula I | 10.0 mg |
| Lactose | 165.0 mg |
| Maize starch | 20.0 mg |
| Talc | 5.0 mg |
| Capsule fill weight | 200.0 mg |

What is claimed is:

1. A compound of formula I

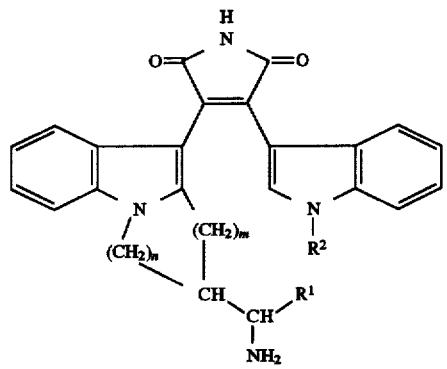

wherein $R^1$ is $C_{3-6}$ alkyl, lower cycloalkyl, aryl or lower aralkyl;

$R^2$ is hydrogen, aryl or lower alkyl optionally substituted by hydroxy, acyloxy, amino, mono(lower alkyl)amino, di(lower alkyl)amino, carboxy, lower alkoxycarbonyl or aminocarbonyl; and m and n are, independently, the numerals 1 or 2, or a pharmaceutically acceptable salt of an acidic compound of formula I with a base or a basic compound of formula I with an acid.

2. A compound according to claim 1, wherein $R^1$ is $C_{3-6}$ alkyl.

3. A compound according to claim 2, wherein $R^2$ is lower alkyl.

4. A compound according to claim 2, wherein m is 1 and n is 2.

5. A compound according to claim 3, wherein m is 1 and n is 2.

6. A compound according to claim 1, 3-[8(S)-[1(R or S)-aminopropyl]-6,7,8,9-tetrahydropyrido[1,2-a]indol-10-yl]-4-(1-methyl-3-indolyl)-1H-pyrrole-2,5-dione.

7. A compound according to claim 1, 3-[8(S)-[1(S)-amino-2-methylpropyl]-6,7,8,9-tetrahydropyrido[1,2-a]indol-10-yl]-4-(1-methyl-3-indolyl)-1H-pyrrole-2,5-dione.

8. A compound according to claim 1, selected from the group consisting of:

- 3-[8(R or S)-1(R or S)-Aminoethyl]-6,7,8,9-tetrahydropyrido[1,2-a]indol-10-yl]-4-(1-methyl-3-indolyl)-1H-pyrrole-2,5-dione,
- 3-[8(R or S)-1(R or S)-aminopropyl]-6,7,8,9-tetrahydropyrido[1,2-a]indol-10-yl]-4-(1-methyl-3-indolyl)-1H-pyrrole-2,5-dione,
- 3-[8(R or S)-1(R or S)-aminobutyl]-6,7,8,9-tetrahydropyrido[1,2-a]indol-10-yl]-4-(1-methyl-3-indolyl)-1H-pyrrole-2,5-dione and
- 3-[8(R or S)-1(R or S)-amino-2-methylpropyl]-6,7,8,9-tetrahydropyrido[1,2-a]indol-10-yl]-4-(1-methyl-3-indolyl)-1H-pyrrole-2,5-dione.

9. A compound according to claim 1, selected from the group consisting of:

- 3-[8(S)-1(R)-Amino-2-methylpropyl]-6,7,8,9-tetrahydropyrido[1,2-a]indol-10-yl]-4-(1-methyl-3-indolyl)-1H-pyrrole-2,5-dione,
- 3-[8(R or S)-[alpha (R or S)-aminobenzyl]-6,7,8,9-tetrahydropyrido[1,2-a]indol-10-yl]-4-(1-methyl-3-indolyl)-1H-pyrrole-2,5-dione,
- 3-[8(S)-[(R or S)-(amino)(cyclopentyl)methyl-6,7,8,9-tetrahydropyrido[1,2-a]indol-10-yl]-4-(1-methyl-3-indolyl)-1H-pyrrole-2,5-dione, 3-[2(R or S)-[1(R or S)-amino-2-methylpropyl]-2,3-dihydro-1H-pyrrolo[1,2-a]indol-9-yl]-4-(1-methyl-3-indolyl)-1H-pyrrole-2,5-dione, 3-[8(RS)-[1(RS)-amino-2-methylpropyl]-7,8,9,10-tetrahydro-6H-azepino[1,2-a]indol-11-yl]-4-(1-methyl-3-indolyl)-1H-pyrrole-2,5-dione, 3-[7(RS)-[1(RS)-amino-2-methylpropyl]-6,7,8,9-tetrahydropyrido[1,2-a]indol-9-yl]-4-(1-methyl-3-indolyl)-1H-pyrrole-2,5-dione and 3-[8(S)-[1(S)-amino-2-methylpropyl]-6,7,8,9-tetrahydropyrido-[1,2-a]indol-10-yl]-4-(1-phenyl-3-indolyl)-1H-pyrrole-2,5-dione.

10. A compound of the formula

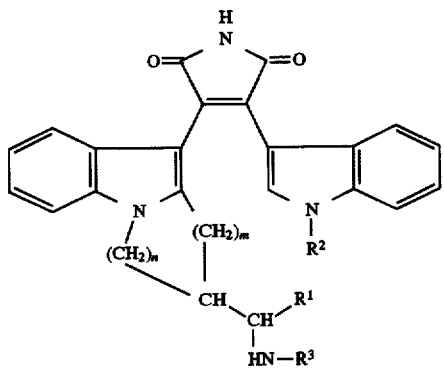

wherein $R^1$ is $C_{3-6}$ alkyl, lower cycloalkyl, aryl or lower aralkyl;

$R^2$ is hydrogen, aryl or lower alkyl optionally substituted by hydroxy, acyloxy, amino, mono(lower alkyl)amino, di(lower alkyl)amino, carboxy, lower alkoxycarbonyl or aminocarbonyl; $R^3$ is a urethane protecting group; and m and n are, independently, the numerals 1 or 2.

11. A pharmaceutical composition which comprises a therapeutically effective amount of a compound of formula I

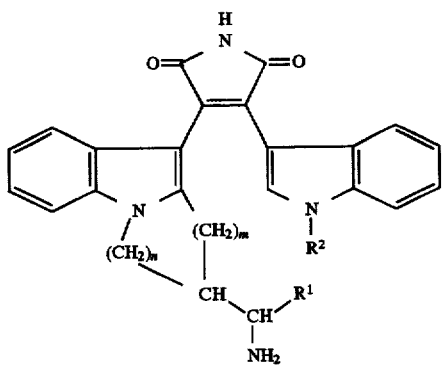

wherein $R^1$ is $C_{1-6}$ alkyl, lower cycloalkyl, aryl or lower aralkyl;

$R^2$ is hydrogen, aryl or lower alkyl optionally substituted by hydroxy, acyloxy, amino, mono(lower alkyl)amino, di(lower alkyl)amino, carboxy, lower alkoxycarbonyl or aminocarbonyl; and m and n are, independently, the numerals 1 or 2, or a pharmaceutically acceptable salt of an acidic compound of formula I with a base or a basic compound of formula I with an acid, and an inert carrier material.

12. A pharmaceutical composition according to claim 11, wherein $R^1$ is $C_{1-6}$ alkyl.

13. A pharmaceutical composition according to claim 11, wherein $R^2$ is lower alkyl.

14. A pharmaceutical composition according to claim 12, wherein m is 1 and n is 2.

15. A pharmaceutical composition according to claim 13, wherein m is 1 and n is 2.

16. A pharmaceutical composition according to claim 11, wherein the compound of formula I is 3-[8(S)-[1(R or S)-amino-propyl]-6,7,8,9-tetrahydropyrido[1,2-a]indol-10-yl]-4-(1-methyl-3-indolyl)-1H-pyrrole-2,5-dione.

17. A pharmaceutical composition according to claim 11, wherein the compound of formula I is 3-[8(S)-[1(S)-amino-2-methylpropyl]-6,7,8,9-tetrahydropyrido[1,2-a]indol-10-yl]-4-(1-methyl-3-indolyl)-1H-pyrrole-2,5-dione.

18. A pharmaceutical composition according to claim 11, wherein the compound of formula I is selected from the group consisting of:

3-[8(R or S)-1(R or S)-Aminoethyl]-6,7,8,9-tetrahydropyrido[1,2-a]indol-10-yl]-4-(1-methyl-3-indolyl)-1H-pyrrole-2,5-dione, 3-[8(R or S)-1(R or S)-aminopropyl]-6,7,8,9-tetrahydropyrido[1,2-a]indol-10-yl]-4-(1-methyl-3-indolyl)-1H-pyrrole-2,5-dione, 3-[8(R or S)-1(R or S)-aminobutyl]-6,7,8,9-tetrahydropyrido[1,2-a]indol-10-yl]-4-(1-methyl-3-indolyl)-1H-pyrrole-2,5-dione and 3-[8(R or S)-1(R or S)-amino-2-methylpropyl]-6,7,8,9-tetrahydropyrido[1,2-a]indol-10-yl]-4-(1-methyl-3-indolyl)-1H-pyrrole-2,5-dione.

19. A pharmaceutical composition according to claim 11, wherein the compound of formula I is selected from the group consisting of:

3-[8(S)-1(R)-amino-2-methylpropyl]-6,7,8,9-tetrahydropyrido[1,2-a]indol-10-yl]-4-(1-methyl-3-indolyl)-1H-pyrrole-2,5-dione, 3-[8(R or S)-[alpha (R or S)-aminobenzyl]-6,7,8,9-tetrahydropyrido[1,2-a]indol-10-yl]-4-(1-methyl-3-indolyl)-1H-pyrrole-2,5-dione, 3-[8(S)-[(R or S)-(amino)(cyclopentyl)methyl-6,7,8,9-tetrahydropyrido[1,2-a]indol-10-yl]-4-(1-methyl-3-indolyl)-1H-pyrrole-2,5-dione, 3-[2(R or S)-[1(R or S)-amino-2-methylpropyl]-2,3-dihydro-1H-pyrrolo[1,2-a]indol-9-yl]-4-(1-methyl-3-indolyl)-1H-pyrrole-2,5-dione, 3-[8(RS)-[1(RS)-amino-2-methylpropyl]-7,8,9,10-tetrahydro-6H-azepino[1,2-a]indol-11-yl]-4-(1-methyl-3-indolyl)-1H-pyrrole-2,5-dione, 3-[7(RS)-[1(RS)-amino-2-methylpropyl]-6,7,8,9-tetrahydropyrido[1,2-a]indol-9-yl]-4-(1-methyl-3-indolyl)-1H-pyrrole-2,5-dione and 3-[8(S)-[1(S)-amino-2-methylpropyl]-6,7,8,9-tetrahydropyrido[1,2-a]indol-10-yl]-4-(1-phenyl-3-indolyl)-1H-pyrrole-2,5-dione.

20. A compound according to claim 1, wherein $R^1$ is propyl, isopropyl, butyl, sec.butyl, tert.butyl or pentyl.

21. A compound according to claim 20, wherein $R^2$ is lower alkyl.

22. A pharmaceutical composition according to claim 11, wherein $R^1$ is propyl, isopropyl, butyl, sec.butyl, tert.butyl or pentyl.

23. A pharmaceutical composition according to claim 22, wherein $R^2$ is lower alkyl.

* * * * *

UNITED STATES PATENT AND TRADEMARK OFFICE
CERTIFICATE OF CORRECTION

PATENT NO. : 5,721,230
DATED : February 24, 1998
INVENTOR(S) : Harris, et al

It is certified that error appears in the above-identified patent and that said Letters Patent is hereby corrected as shown below:

In the Claims

Please delete Claim 6, Column 30, lines 35-38.

Please delete the first two compounds in Claim 8, Column 30, lines 44-49 as follows:

"3-[8(R or S)-1(R or S)-Aminoethyl]-6,7,8,9- tetrahydropyrido[1,2-a]indol-10-yl]

-4-(1-methyl-3-indolyl)-1H-pyrrole-2,5-dione,

3-[8(R or S)-1(R or S)-aminopropyl]-6,7,8,9- tetrahydropyrido[1,2-a]indol-10-yl]

-4-(1-methyl-3-indolyl)-1H-pyrrole-2,5-dione," .

UNITED STATES PATENT AND TRADEMARK OFFICE
CERTIFICATE OF CORRECTION

PATENT NO. : 5,721,230
DATED : February 24, 1998
INVENTOR(S) : Harris, et al.

It is certified that error appears in the above-identified patent and that said Letters Patent is hereby corrected as shown below:

Please delete Claim 16, Column 32, lines 7-10.

Please delete the first two compounds in Claim 18, Column 33, lines 18-23 as follows:

"3-[8(R or S)-1(R or S)-Aminoethyl]-6,7,8,9- tetrahydropyrido[1,2-a]indol-10-yl]

-4-(1-methyl-3-indolyl)-1H-pyrrole-2,5-dione,

3-[8(R or S)-1(R or S)-aminopropyl]-6,7,8,9- tetrahydropyrido[1,2-a]indol-10-yl]

-4-(1-methyl-3-indolyl)-1H-pyrrole-2,5-dione,".

Signed and Sealed this

Twenty-third Day of June, 1998

Attest:

BRUCE LEHMAN

Attesting Officer

Commissioner of Patents and Trademarks